US000001838H

United States Statutory Invention Registration [19]

[11] Reg. Number: H1,838

Cullen et al.

[45] Published: Feb. 1, 2000

[54] INSECTICIDAL N-(ARYLALKYL)-4-[BIS (SUBSTITUTED ARYL)HYDROXYMETHYL] AZABICYCLO[3.3.1.]NONANES AND [3.2.1.] OCTANES

[75] Inventors: Thomas G. Cullen, Milltown; Ian Robert Silverman, Moorestown, both of N.J.; Walter H. Yeager, Yardley, Pa.

[73] Assignee: FMC Corporation

[21] Appl. No.: 09/212,223

[22] Filed: Dec. 16, 1998

Related U.S. Application Data

[60] Provisional application No. 60/068,001, Dec. 17, 1997.

[51] Int. Cl.[7] ..... A01N 43/42

[52] U.S. Cl. ..... 514/299; 514/304; 546/112; 546/114

[58] Field of Search ..... 546/124, 112; 514/304, 299

[56] References Cited

FOREIGN PATENT DOCUMENTS 2319524 5/1998 United Kingdom .

*Primary Examiner*—Harold J. Tudor
*Attorney, Agent, or Firm*—Donald J. Silvert; I. Robert Silverman; Marcia D. Pintzuk

[57] ABSTRACT

Compounds for control of insects and arcarids are disclosed and exemplified which are N-(arylalkyl)-4-[bis(substituted aryl)hydroxymethyl]azabicyclo[3.3. 1 .]nonanes and [3.2.1.] octanes, including N-oxides thereof, N-(substituted-oxy) derivatives thereof, and agriculturally acceptable salts thereof, having the formula:

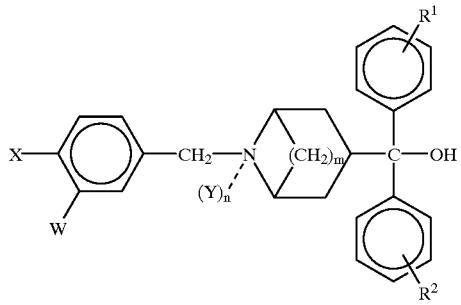

Certain novel intermediates for these pesticidal compounds are also disclosed.

6 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

INSECTICIDAL N-(ARYLALKYL)-4-[BIS (SUBSTITUTED ARYL)HYDROXYMETHYL] AZABICYCLO[3.3.1.]NONANES AND [3.2.1.] OCTANES

This application claims benefit of provisional application Ser. No. 60/068,001 filed Dec. 17, 1997.

The present invention relates to novel pesticidal compounds, intermediates therefor, formulations thereof, and to methods for controlling insects, acarids and the like. In particular, the invention relates to certain N-( arylalkyl)-4-[bis(substituted aryl)hydroxymethyl]azabicyclo[3.3.1.] nonanes and [3.2.1.]octanes, to methods for control of insects with such compounds or formulations thereof, and to certain novel intermediates in the preparation of such insecticidal compounds.

In general the compounds of this invention are N-(substituted arylalkyl) 4-[bis(substituted aryl) hydroxymethyl]azabicyclo[3.3.1.]nonanes and [3.2.1.] octanes, their N-oxides, N-(substituted-oxy) derivatives thereof, and agriculturally acceptable salts thereof. More particularly the compounds of this invention are compounds of the formula:

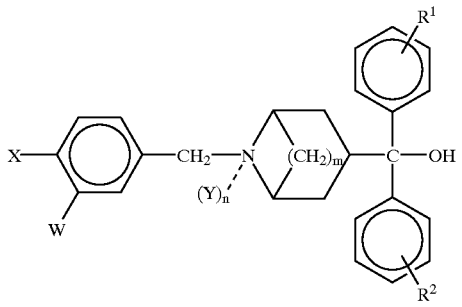

in which m is 2 or 3;

n is 0 or 1;

W is hydrogen or alkoxy;

X is hydrogen, alkoxy, cycloalkylalkoxy, alkoxycarbonyl, alkoxycarbonylamino, alkoxyimino, haloalkoxyimino, or a five-or six-membered heteroaryl or heteroaryloxy in which one or more hetero atoms may be optionally substituted with an alkyl;

$R^1$ and $R^2$ are independently selected from hydrogen, haloalkyl, halothio, or haloalkoxy; and When n is 1, Y represents (a) an N-oxide of the ring nitrogen or (b) an agriculturally acceptable anionic salt of the ring nitrogen; or (c) forms an $OR^3$ linkage in which $R^3$ is selected from hydrogen, alkyl, alkoxycarbonylalkyl, hydroxycarbonylethyl, in association with an agriculturally acceptable anion resulting in an anionic salt, or $R^3$ is an oxycarbonylalkyl group bearing a negative charge resulting in an inner salt.

Unless otherwise specifically indicated to the contrary, the foregoing terms have the following meanings. "Alkyl" means lower alkyl having 1 to 4 carbon atoms which may have a branched or unbranched chain. "Heteroaryl" refers to an aromatic (unsaturated) ring structure having 1 to 4 nitrogen atoms as hetero ring components, the balance being carbon atoms. "Halo" or "halide" refers to one or more halogen atoms selected from chlorine, fluorine, bromine or iodine, with fluorine being the preferred atom when appended to an alkyl or this group. "Anion", "anionic" or "anionic salt" refers to negatively charged ions which form salts with a positively charged ring nitrogen, including but not limited to, halides, salicylates and alkylsulfonates.

Of the compounds described above, the preferred insecticidal compounds are those wherein W is hydrogen; X is propoxy, methoxycarbonylamino, or 2-ethyltetrazol-5-yl; $R^1$ and $R^2$ are 4-trifluoromethyl or 4-trifluoromethoxy; and $R^3$ is methyl or ethoxycarbonylethyl in association with an agriculturally acceptable anionic salt, or an oxycarbonylalkyl group bearing a negative charge resulting in an inner salt.

The following are novel intermediates of the invention:

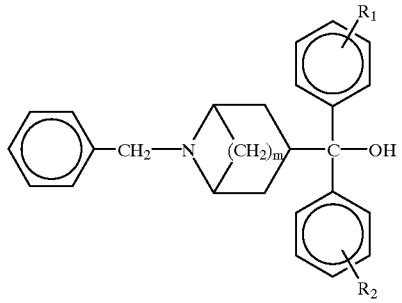

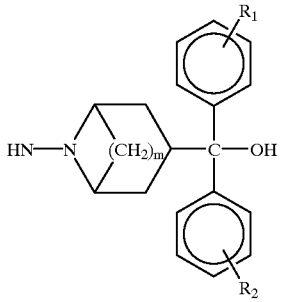

in which m is 2 or 3; and $R^1$ and $R^2$ are 4-trifluoromethyl or 4-trifluoromethoxy.

The insecticidal compounds of the present invention may be prepared by methods known to one skilled in the art. A suitable route for preparation of these compounds are shown in Schema 1 set forth below.

As depicted in Schema 1, an appropriately substituted phenylmethyl azabicycloalkan-3-one (SM 1) was reacted with tosylmethyl isocyanide under basic conditions to form the appropriate 3-cyanophenylmethylazabicycloalkane (A). The nitrile (A) was in turn treated with an alcohol, for example ethanol, in the presence of hydrogen chloride gas, yielding the appropriate alkyl N-(substituted phenylmethylazabicycloalkyl)carboxylate (B), for example ethyl N-(9-phenylmethyl-9-azabicyclo[3.3.1]nonane-3-yl) carboxylate. The so-prepared alkyl carboxylate (B) was then reacted with a two or three molar excess of the Grignard reagent of an appropriately substituted halide, for example 1-trifluoromethyl-4-bromobenzene, to form the targeted phenylmethyl-α,α-bis(substituted phenyl)azabicycloalkane-3-methanol (I), for example 9-phenyhnethyl-α,α-bis(4-trifluoromethylphenyl)-9-azabicyclo[3.3.1.]nonane-3-methanol. Example 1 provides the detailed procedure for this route.

The methanol (I) was reacted with hydrogen chloride gas in the presence of diethyl ether and then hydrogenated with methanol in the presence of 10% palladium on carbon, affording the targeted α,α-bis(substituted phenyl) azabicycloalkane-3-methanol (II). The α,α-bis(substituted phenyl)azabicycloalkane-3-methanol (II) was then reacted with the appropriately substituted phenylmethyl halide, for example 4-propoxyphenylmethyl chloride, affording the targeted (substituted phenyl)methyl-α,α-bis(substituted phenyl)azabicycloalkane-3-methanol (III), for example 9-(4-propoxyphenyl)methyl-α,α-bis(4-trifluoromethylphenyl)-9-azabicyclo[3.3.1.]nonane-3-methanol. The 3-methanol (III) (can then be reacted with an oxidizing agent, such as hydrogen peroxide or 3-chloroperoxybenzoic acid, to yield the targeted (substituted phenyl)methyl-α,α-bis(substituted phenyl)-azabicycloalkane-3 -methanol N-oxide (IV), for example 9-(4-propoxyphenyl)methyl-α,α-bis(4-trifluoromethylphenyl)-9-azabicyclo[3.3.1.]nonane-3-methanol N-oxide. The methanol (III) can also be reacted with the appropriate acids, such as hydrochloric or ethanesulfonic acid, yielding the targeted salts (V). Additional salts (VI) can be prepared by reacting the N-oxide (IV) with an appropriate halide, such as 3-bromopropionic acid, or with a sulfate or sulfonate. Even more salts (VII) can be prepared by reacting the N-oxide (IV) with the appropriate acid, such as hydrochloric, ethanesulfonic, or salicylic. Examples 2, 3, 4, 5, 6, and 7 described the detailed procedures for this route.

Schema 1

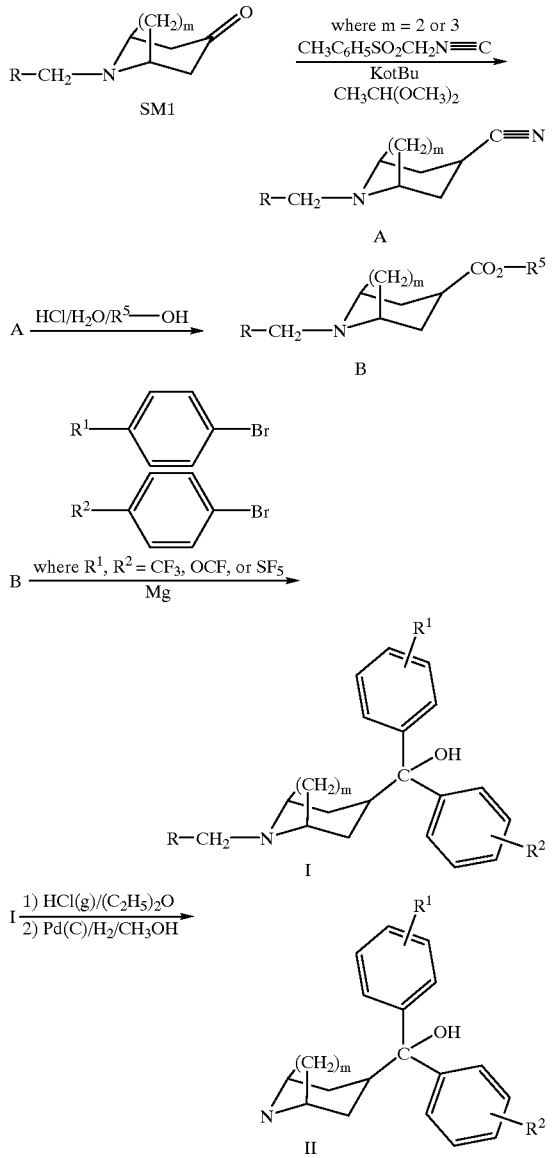

-continued

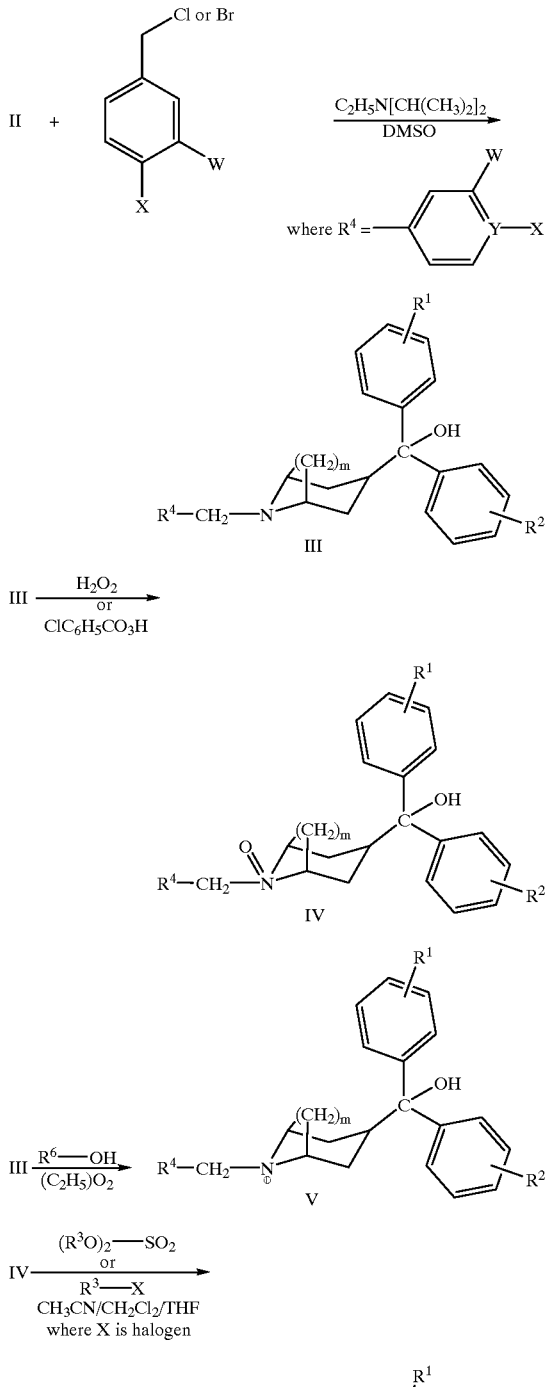

-continued

IV $\xrightarrow{\text{Acid}}$

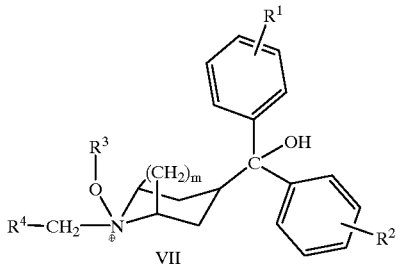

VII

Tables 1, 2, 3 and 4 below illustrate the insecticidal compounds of this invention.

TABLE 1

Insecticidal N-(Phenylmethylazabicyclo)benzhydryl Alcohols

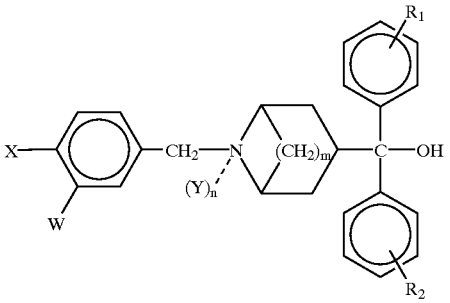

N---Y is N-Oxide when n is 1

| No. | W | X | $R^1$ | $R^2$ | n |
|---|---|---|---|---|---|
| 1 | H | H | 3 4-$CF_3$ | 4-$CF_3$ | 0 |
| 2 | H | $OC_3H_7$ | 3 4-$CF_3$ | 4-$CF_3$ | 0 |
| 3 | H | $OC_3H_7$ | 3 4-$CF_3$ | 4-$CF_3$ | 1 |
| 4 | H | H | 2 4-$OCF_3$ | 4-$OCF_3$ | 0 |
| 5 | H | $OC_2H_5$ | 2 4-$OCF_3$ | 4-$OCF_3$ | 0 |
| 6 | H | $OC_3H_7$ | 2 4-$OCF_3$ | 4-$OCF_3$ | 0 |
| 7 | H | $OC_3H_7$ | 2 4-$OCF_3$ | 4-$OCF_3$ | 1 |
| 8 | H | $OC_4H_9$ | 2 4-$OCF_3$ | 4-$OCF_3$ | 0 |
| 9 | H | $NHCO_2CH_3$ | 2 4-$OCF_3$ | 4-$OCF_3$ | 0 |
| 10 | —$OC_3H_7$ | H | 2 4-$OCF_3$ | 4-$OCF_3$ | 0 |
| 11 | H | $CO_2CH(CH_3)_2$ | 2 4-$CF_3$ | 4-$CF_3$ | 0 |
| 12 | H | $CO_2CH(CH_3)_2$ | 3 4-$CF_3$ | 4-$CF_3$ | 1 |
| 13 | H | $CO_2CH(CH_3)_2$ | 3 4-$CF_3$ | 4-$CF_3$ | 0 |
| 14 | H | $CO_2CH(CH_3)_2$ | 3 4-$CF_3$ | 4-$CF_3$ | 1 |
| 15 | H | $CO_2CH(CH_3)_2$ | 2 4-$OCF_3$ | 4-$OCF_3$ | 0 |
| 16 | H | $CO_2CH(CH_3)_2$ | 2 4-$OCF_3$ | 4-$OCF_3$ | 1 |
| 17 | H | $CO_2CH(CH_3)_2$ | 3 4-$OCF_3$ | 4-$OCF_3$ | 0 |
| 18 | H | $CO_2CH(CH_3)_2$ | 3 4-$OCF_3$ | 4-$OCF_3$ | 1 |
| 19 | H | $CO_2CH(CH_3)_2$ | 2 4-$SF_5$ | 4-$SF_5$ | 0 |
| 20 | H | $CO_2CH(CH_3)_2$ | 2 4-$SF_5$ | 4-$SF_5$ | 1 |
| 21 | H | $CO_2CH(CH_3)_2$ | 3 4-$SF_5$ | 4-$SF_5$ | 0 |
| 22 | H | $CO_2CH(CH_3)_2$ | 3 4-$SF_5$ | 4-$SF_5$ | 1 |
| 23 | H | $NHCO_2CH_3$ | 2 4-$CF_3$ | 4-$CF_3$ | 0 |
| 24 | H | $NHCO_2CH_3$ | 2 4-$CF_3$ | 4-$CF_3$ | 1 |
| 25 | H | $NHCO_2CH_3$ | 3 4-$CF_3$ | 4-$CF_3$ | 0 |
| 26 | H | $NHCO_2CH_3$ | 3 4-$CF_3$ | 4-$CF_3$ | 1 |
| 27 | H | $NHCO_2CH_3$ | 2 4-$OCF_3$ | 4-$OCF_3$ | 0 |
| 28 | H | $NHCO_2CH_3$ | 2 4-$OCF_3$ | 4-$OCF_3$ | 1 |
| 29 | H | $NHCO_2CH_3$ | 3 4-$OCF_3$ | 4-$OCF_3$ | 0 |
| 30 | H | $NHCO_2CH_3$ | 3 4-$OCF_3$ | 4-$OCF_3$ | 1 |
| 31 | H | $NHCO_2CH_3$ | 2 4-$SF_5$ | 4-$SF_5$ | 0 |
| 32 | H | $NHCO_2CH_3$ | 2 4-$SF_5$ | 4-$SF_5$ | 1 |
| 33 | H | $NHCO_2CH_3$ | 3 4-$SF_5$ | 4-$SF_5$ | 0 |
| 34 | H | $NHCO_2CH_3$ | 3 4-$SF_5$ | 4-$SF_5$ | 1 |
| 35 | H | $NHCO_2CH_3$ | 2 4-$CF_3$ | 4-$CF_3$ | 0 |
| 36 | H | $NHCO_2CH(CH_3)_2$ | 2 4-$CF_3$ | 4-$CF_3$ | 1 |
| 37 | H | $NHCO_2CH(CH_3)_2$ | 3 4-$CF_3$ | 4-$CF_3$ | 0 |
| 38 | H | $NHCO_2CH(CH_3)_2$ | 3 4-$CF_3$ | 4-$CF_3$ | 1 |

TABLE 1-continued

Insecticidal N-(Phenylmethylazabicyclo)benzhydryl Alcohols

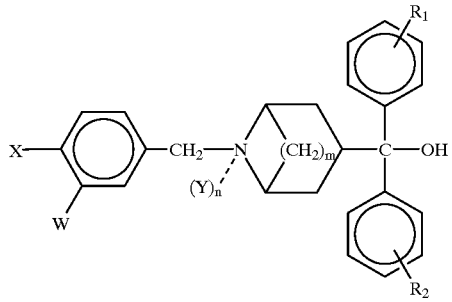

N---Y is N-Oxide when n is 1

| No. | W | X | $R^1$ | $R^2$ | n |
|---|---|---|---|---|---|
| 39 | H | $NHCO_2CH(CH_3)_2$ | 2 4-$OCF_3$ | 4-$OCF_3$ | 0 |
| 40 | H | $NHCO_2CH(CH_3)_2$ | 2 4-$OCF_3$ | 4-$OCF_3$ | 1 |
| 41 | H | $NHCO_2CH(CH_3)_2$ | 3 4-$OCF_3$ | 4-$OCF_3$ | 0 |
| 42 | H | $NHCO_2CH(CH_3)_2$ | 3 4-$OCF_3$ | 4-$OCF_3$ | 1 |
| 43 | H | $NHCO_2CH(CH_3)_2$ | 2 4-$SF_5$ | 4-$SF_5$ | 0 |
| 44 | H | $NHCO_2CH(CH_3)_2$ | 2 4-$SF_5$ | 4-$SF_5$ | 1 |
| 45 | H | $NHCO_2CH(CH_3)_2$ | 3 4-$SF_5$ | 4-$SF_5$ | 0 |
| 46 | H | $NHCO_2CH(CH_3)_2$ | 3 4-$SF_5$ | 4-$SF_5$ | 1 |
| 47 | H | 2-methyltetrazol-5-yl | 2 4-$CF_3$ | 4-$CF_3$ | 0 |
| 48 | H | 2-methyltetrazol-5-yl | 2 4-$CF_3$ | 4-$CF_3$ | 1 |
| 49 | H | 2-methyltetrazol-5-yl | 3 4-$CF_3$ | 4-$CF_3$ | 0 |
| 50 | H | 2-methyltetrazol-5-yl | 3 4-$CF_3$ | 4-$CF_3$ | 1 |
| 51 | H | 2-methyltetrazol-5-yl | 2 4-$OCF_3$ | 4-$OCF_3$ | 0 |
| 52 | H | 2-methyltetrazol-5-yl | 2 4-$OCF_3$ | 4-$OCF_3$ | 1 |
| 53 | H | 2-methyltetrazol-5-yl | 3 4-$OCF_3$ | 4-$OCF_3$ | 0 |
| 54 | H | 2-methyltetrazol-5-yl | 3 4-$OCF_3$ | 4-$OCF_3$ | 1 |
| 55 | H | 2-methyltetrazol-5-yl | 2 4-$SF_5$ | 4-$SF_5$ | 0 |
| 56 | H | 2-methyltetrazol-5-yl | 2 4-$SF_5$ | 4-$SF_5$ | 1 |
| 57 | H | 2-methyltetrazol-5-yl | 3 4-$SF_5$ | 4-$SF_5$ | 0 |
| 58 | H | 2-methyltetrazol-5-yl | 3 4-$SF_5$ | 4-$SF_5$ | 1 |
| 59 | H | 2-ethyltetrazol-5-yl | 2 4-$CF_3$ | 4-$CF_3$ | 0 |
| 60 | H | 2-ethyltetrazol-5-yl | 2 4-$CF_3$ | 4-$CF_3$ | 1 |
| 61 | H | 2-ethyltetrazol-5-yl | 3 4-$CF_3$ | 4-$CF_3$ | 0 |
| 62 | H | 2-ethyltetrazol-5-yl | 3 4-$CF_3$ | 4-$CF_3$ | 1 |
| 63 | H | 2-ethyltetrazol-5-yl | 2 4-$OCF_3$ | 4-$OCF_3$ | 0 |
| 64 | H | 2-ethyltetrazol-5-yl | 2 4-$OCF_3$ | 4-$OCF_3$ | 1 |
| 65 | H | 2-ethyltetrazol-5-yl | 3 4-$OCF_3$ | 4-$OCF_3$ | 0 |
| 66 | H | 2-ethyltetrazol-5-yl | 3 4-$OCF_3$ | 4-$OCF_3$ | 1 |
| 67 | H | 2-ethyltetrazol-5-yl | 2 4-$SF_5$ | 4-$SF_5$ | 0 |
| 58 | H | 2-ethyltetrazol-5-yl | 2 4-$SF_5$ | 4-$SF_5$ | 1 |
| 69 | H | 2-ethyltetrazol-5-yl | 3 4-$SF_5$ | 4-$SF_5$ | 0 |
| 70 | H | 2-ethyltetrazol-5-yl | 3 4-$SF_5$ | 4-$SF_5$ | 1 |
| 71 | H | pyrid-2-yl | 2 4-$CF_3$ | 4-$CF_3$ | 0 |
| 72 | H | pyrid-2-yl | 2 4-$CF_3$ | 4-$CF_3$ | 1 |
| 73 | H | pyrid-2-yl | 3 4-$CF_3$ | 4-$CF_3$ | 0 |
| 74 | H | pyrid-2-yl | 3 4-$CF_3$ | 4-$CF_3$ | 1 |
| 75 | H | pyrid-2-yl | 2 4-$OCF_3$ | 4-$OCF_3$ | 0 |
| 76 | H | pyrid-2-yl | 2 4-$OCF_3$ | 4-$OCF_3$ | 1 |
| 77 | H | pyrid-2-yl | 3 4-$OCF_3$ | 4-$OCF_3$ | 0 |
| 78 | H | pyrid-2-yl | 3 4-$OCF_3$ | 4-$OCF_3$ | 1 |
| 79 | H | pyrid-2-yl | 2 4-$SF_5$ | 4-$SF_5$ | 0 |
| 80 | H | pyrid-2-yl | 2 4-$SF_5$ | 4-$SF_5$ | 1 |
| 81 | H | pyrid-2-yl | 3 4-$SF_5$ | 4-$SF_5$ | 0 |
| 82 | H | pyrid-2-yl | 3 4-$SF_5$ | 4-$SF_5$ | 1 |
| 83 | H | pyrid-2-yloxy | 2 4-$CF_3$ | 4-$CF_3$ | 0 |
| 84 | H | pyrid-2-yloxy | 2 4-$CF_3$ | 4-$CF_3$ | 1 |
| 85 | H | pyrid-2-yloxy | 3 4-$CF_3$ | 4-$CF_3$ | 0 |
| 86 | H | pyrid-2-yloxy | 3 4-$CF_3$ | 4-$CF_3$ | 1 |
| 87 | H | pyrid-2-yloxy | 2 4-$OCF_3$ | 4-$OCF_3$ | 0 |
| 88 | H | pyrid-2-yloxy | 2 4-$OCF_3$ | 4-$OCF_3$ | 1 |
| 89 | H | pyrid-2-yloxy | 3 4-$OCF_3$ | 4-$OCF_3$ | 0 |
| 90 | H | pyrid-2-yloxy | 3 4-$OCF_3$ | 4-$OCF_3$ | 1 |
| 91 | H | pyrid-2-yloxy | 2 4-$SF_5$ | 4-$SF_5$ | 0 |
| 92 | H | pyrid-2-yloxy | 2 4-$SF_5$ | 4-$SF_5$ | 1 |
| 93 | H | pyrid-2-yloxy | 3 4-$SF_5$ | 4-$SF_5$ | 0 |
| 94 | H | pyrid-2-yloxy | 3 4-$SF_5$ | 4-$SF_5$ | 1 |
| 95 | H | cyclopropylmethoxy | 2 4-$CF_3$ | 4-$CF_3$ | 0 |

TABLE 1-continued

Insecticidal N-(Phenylmethylazabicyclo)benzhydryl Alcohols

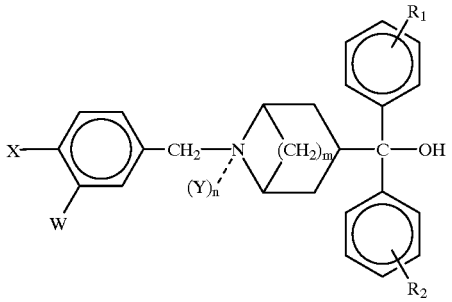

N---Y is N-Oxide when n is 1

| No. | W | X | $R^1$ | $R^2$ | n |
|---|---|---|---|---|---|
| 96 | H | cyclopropylmethoxy | 2 4-$CF_3$ | 4-$CF_3$ | 1 |
| 97 | H | cyclopropylmethoxy | 3 4-$CF_3$ | 4-$CF_3$ | 0 |
| 98 | H | cyclopropylmethoxy | 3 4-$CF_3$ | 4-$CF_3$ | 1 |
| 99 | H | cyclopropylmethoxy | 2 4-$OCF_3$ | 4-$OCF_3$ | 0 |
| 100 | H | cyclopropylmethoxy | 2 4-$OCF_3$ | 4-$OCF_3$ | 1 |
| 101 | H | cyclopropylmethoxy | 3 4-$OCF_3$ | 4-$OCF_3$ | 0 |
| 102 | H | cyclopropylmethoxy | 3 4-$OCF_3$ | 4-$OCF_3$ | 1 |
| 103 | H | cyclopropylmethoxy | 2 4-$SF_5$ | 4-$SF_5$ | 0 |
| 104 | H | cyclopropylmethoxy | 2 4-$SF_5$ | 4-$SF_5$ | 1 |
| 105 | H | cyclopropylmethoxy | 3 4-$SF_5$ | 4-$SF_5$ | 0 |
| 106 | H | cyclopropylmethoxy | 3 4-$SF_5$ | 4-$SF_5$ | 1 |
| 107 | H | N═O—$CH_3$ | 3 4-$CF_3$ | 4-$CF_3$ | 0 |
| 108 | H | N═O—$CH_3$ | 2 4-$CF_3$ | 4-$CF_3$ | 0 |
| 109 | H | N═O—$CH_3$ | 3 4-$CF_3$ | 4-$CF_3$ | 1 |
| 110 | H | N═O—$CH_3$ | 2 4-$CF_3$ | 4-$CF_3$ | 1 |
| 111 | H | N═O—$CH_3$ | 3 4-$OCF_3$ | 4-$OCF_3$ | 0 |
| 112 | H | N═O—$CH_3$ | 3 4-$OCF_3$ | 4-$OCF_3$ | 1 |
| 113 | H | N═O—$CH_2CH_3$ | 3 4-$CF_3$ | 4-$CF_3$ | 0 |
| 114 | H | N═O—$CH_2CH_3$ | 3 4-$CF_3$ | 4-$CF_3$ | 1 |
| 115 | H | N═O—$CH_2CH_3$ | 3 4-$OCF_3$ | 4-$OCF_3$ | 0 |
| 116 | H | N═O—$CH_2CH_3$ | 3 4-$OCF_3$ | 4-$OCF_3$ | 1 |
| 117 | H | N═O—$CH_2CH_3F$ | 3 4-$OCF_3$ | 4-$OCF_3$ | 0 |

TABLE 2

Salts of Insecticidal N-(Phenylmethylazabicyclo)benzhydryl Alcohols

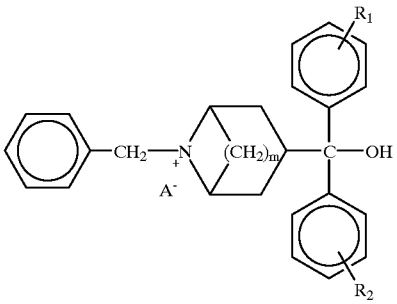

| No. | X | m | $R^1$ | $R^2$ | $A^-$ |
|---|---|---|---|---|---|
| 118 | $OC_3H_7$ | 3 | 4-$CF_3$ | 4-$CF_3$ | Chloride |
| 119 | $OC_3H_7$ | 3 | 4-$CF_3$ | 4-$CF_3$ | Ethylsulfonate |
| 120 | $CO_2CH(CH_3)_2$ | 2 | 4-$CF_3$ | 4-$CF_3$ | Chloride |
| 121 | $CO_2CH(CH_3)_2$ | 2 | 4-$CF_3$ | 4-$CF_3$ | Ethylsulfonate |
| 122 | $CO_2CH(CH_3)_2$ | 3 | 4-$CF_3$ | 4-$CF_3$ | Chloride |
| 123 | $CO_2CH(CH_3)_2$ | 3 | 4-$CF_3$ | 4-$CF_3$ | Ethylsulfonate |
| 124 | $CO_2CH(CH_3)_2$ | 2 | 4-$OCF_3$ | 4-$OCF_3$ | Chloride |
| 125 | $CO_2CH(CH_3)_2$ | 2 | 4-$OCF_3$ | 4-$OCF_3$ | Ethylsulfonate |
| 126 | $CO_2CH(CH_3)_2$ | 3 | 4-$OCF_3$ | 4-$OCF_3$ | Chloride |

TABLE 2-continued

Salts of Insecticidal N-(Phenylmethylazabicyclo)benzhydryl Alcohols

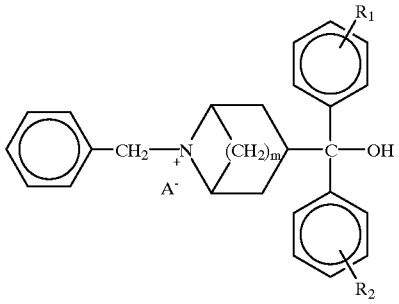

| No. | X | m | $R^1$ | $R^2$ | $A^-$ |
|---|---|---|---|---|---|
| 127 | $CO^2CH(CH_3)_2$ | 3 | 4-$OCF_3$ | 4-$OCF_3$ | Ethylsulfonate |
| 128 | $NHCO_2CH_3$ | 2 | 4-$CF_3$ | 4-$CF_3$ | Chloride |
| 129 | $NHCO_2CH_3$ | 2 | 4-$CF_3$ | 4-$CF_3$ | Ethylsulfonate |
| 130 | $NHCO_2CH_3$ | 3 | 4-$CF_3$ | 4-$CF_3$ | Chloride |
| 131 | $NHCO_2CH_3$ | 3 | 4-$CF_3$ | 4-$CF_3$ | Ethylsulfonate |
| 132 | $NHCO_2CH_3$ | 2 | 4-$OCF_3$ | 4-$OCF_3$ | Chloride |
| 133 | $NHCO_2CH_3$ | 2 | 4-$OCF_3$ | 4-$OCF_3$ | Ethylsulfonate |
| 134 | $NHCO_2CH_3$ | 3 | 4-$OCF_3$ | 4-$OCF_3$ | Chloride |
| 135 | $NHCO_2CH_3$ | 3 | 4-$OCF_3$ | 4-$OCF_3$ | Ethylsulfonate |
| 136 | $NHCO_2CH(CH_3)_2$ | 2 | 4-$CF_3$ | 4-$CF_3$ | Chloride |
| 137 | $NHCO_2CH(CH_3)_2$ | 2 | 4-$CF_3$ | 4-$CF_3$ | Ethylsulfonate |
| 138 | $NHCO_2CH(CH_3)_2$ | 3 | 4-$CF_3$ | 4-$CF_3$ | Chloride |
| 139 | $NHCO_2CH(CH_3)_2$ | 3 | 4-$CF_3$ | 4-$CF_3$ | Ethylsulfonate |
| 140 | $NHCO_2CH(CH_3)_2$ | 2 | 4-$OCF_3$ | 4-$OCF_3$ | Chloride |
| 141 | $NHCO_2CH(CH_3)_2$ | 2 | 4-$OCF_3$ | 4-$OCF_3$ | Ethylsulfonate |
| 142 | $NHCO_2CH(CH_3)_2$ | 3 | 4-$OCF_3$ | 4-$OCF_3$ | Chloride |
| 143 | $NHCO_2CH(CH_3)_2$ | 3 | 4-$OCF_3$ | 4-$OCH_3$ | Ethylsulfonate |
| 144 | 2-methyltetrazol-5-yl | 2 | 4-$CF_3$ | 4-$CF_3$ | Chloride |
| 145 | 2-methyltetrazol-5-yl | 2 | 4-$CF_3$ | 4-$CF_3$ | Ethylsulfonate |
| 146 | 2-methyltetrazol-5-yl | 3 | 4-$CF_3$ | 4-$CF_3$ | Chloride |
| 147 | 2-methyltetrazol-5-yl | 3 | 4-$CF_3$ | 4-$CF_3$ | Ethylsulfonate |
| 148 | 2-methyltetrazol-5-yl | 2 | 4-$OCF_3$ | 4-$OCF_3$ | Chloride |
| 149 | 2-methyltetrazol-5-yl | 2 | 4-$OCF_3$ | 4-$OCF_3$ | Ethylsulfonate |
| 150 | 2-methyltetrazol-5-yl | 3 | 4-$OCF_3$ | 4-$OCF_3$ | Chloride |
| 151 | 2-methyltetrazol-5-yl | 3 | 4-$OCF_3$ | 4-$OCF_3$ | Ethylsulfonate |
| 152 | 2-methyltetrazol-5-yl | 2 | 4-$CF_3$ | 4-$CF_3$ | Chloride |
| 153 | 2-ethyltetrazol-5-yl | 2 | 4-$CF_3$ | 4-$CF_3$ | Ethylsulfonate |
| 154 | 2-ethyltetrazol-5-yl | 3 | 4-$CF_3$ | 4-$CF_3$ | Chloride |
| 155 | 2-ethyltetrazol-5-yl | 3 | 4-$CF_3$ | 4-$CF_3$ | Ethylsulfonate |
| 156 | 2-ethyltetrazol-5-yl | 2 | 4-$OCF_3$— | 4-$OCF_3$ | Chloride |
| 157 | 2-ethyltetrazol-5-yl | 2 | 4-$OCF_3$ | 4-$OCF_3$ | Ethylsulfonate |
| 158 | 2-ethyltetrazol-5-yl | 3 | 4-$OCF_3$ | 4-$OCF_3$ | Chloride |
| 159 | 2-ethyltetrazol-5-yl | 3 | 4-$OCF_3$ | 4-$OCF_3$ | Ethylsulfonate |
| 160 | pyrid-2-yl | 2 | 4-$CF_3$ | 4-$CF_3$ | Chloride |
| 161 | pyrid-2-yl | 2 | 4-$CF_3$ | 4-$CF_3$ | Ethylsulfonate |
| 162 | pyrid-2-yl | 3 | 4-$CF_3$ | 4-$CF_3$ | Chloride |
| 163 | pyrid-2-yl | 3 | 4-$CF_3$ | 4-$CF_3$ | Ethylsulfonate |
| 164 | pyrid-2-yl | 2 | 4-$OCF_3$ | 4-$OCF_3$ | Chloride |
| 165 | pyrid-2-yl | 2 | 4-$OCF_3$ | 4-$OCF_3$ | Ethylsulfonate |
| 166 | pyrid-2-yl | 3 | 4-$OCF_3$ | 4-$OCF_3$ | Chloride |
| 167 | pyrid-2-yl | 3 | 4-$OCF_3$ | 4-$OCF_3$ | Ethylsulfonate |
| 168 | pyrid-2-yloxy | 2 | 4-$CF_3$ | 4-$CF_3$ | Chloride |
| 169 | pyrid-2-yloxy | 2 | 4-$CF_3$ | 4-$CF_3$ | Ethylsulfonate |
| 170 | pyrid-2-yloxy | 3 | 4-$CF_3$ | 4-$CF_3$ | Chloride |
| 171 | pyrid-2-yloxy | 3 | 4-$CF_3$ | 4-$CF_3$ | Ethylsulfonate |
| 172 | pyrid-2-yloxy | 2 | 4-$OCF_3$ | 4-$OCF_3$ | Chloride |
| 173 | pyrid-2-yloxy | 2 | 4-$OCF_3$ | 4-$OCF_3$ | Ethylsulfonate |
| 174 | pyrid-2-yloxy | 3 | 4-$OCF_3$ | 4-$OCF_3$ | Chloride |
| 175 | pyrid-2-yloxy | 3 | 4-$OCF_3$ | 4-$OCF_3$ | Ethylsulfonate |
| 176 | cyclopropylmethoxy | 2 | 4-$CF_3$ | 4-$CF_3$ | Chloride |
| 177 | cyclopropylmethoxy | 2 | 4-$CF_3$ | 4-$CF_3$ | Ethylsulfonate |
| 178 | cyclopropylmethoxy | 3 | 4-$CF_3$ | 4-$CF_3$ | Chloride |
| 179 | cyclopropylmethoxy | 3 | 4-$CF_3$ | 4-$CF_3$ | Ethylsulfonate |
| 180 | cyclopropylmethoxy | 2 | 4-$OCF_3$ | 4-$OCF_3$ | Chloride |
| 181 | cyclopropylmethoxy | 2 | 4-$OCF_3$ | 4-$OCF_3$ | Ethylsulfonate |
| 182 | cyclopropylmethoxy | 3 | 4-$OCF_3$ | 4-$OCF_3$ | Chloride |
| 183 | cyclopropylmethoxy | 3 | 4-$OCF_3$ | 4-$OCF_3$ | Ethylsulfonate |
| 184 | ═$NCOCH_2CH_3$ | 3 | 4-$OCF_3$ | 4-$OCF_3$ | Ethylsulfonate |

TABLE 2-continued

Salts of Insecticidal N-(Phenylmethylazabicyclo)benzhydryl Alcohols

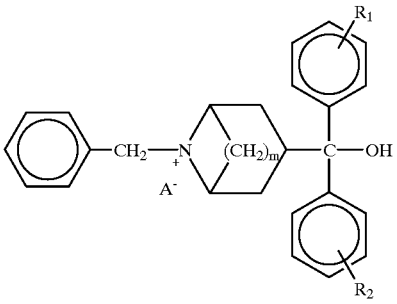

| No. | X | m | $R^1$ | $R^2$ | $A^-$ |
|---|---|---|---|---|---|
| 185 | =NOCH³ | 3 | 4-$OCF_3$ | 4-$OCF_3$ | Ethylsulfonate |
| 186 | =$NOCH_2CH_2F$ | 3 | 4-$OCF_3$ | 4-$OCF_3$ | Ethylsulfonate |
| 187 | =$NOCH_2CH_2F$ | 2 | 4-$OCF_3$ | 4-$OCF_3$ | Ethylsulfonate |
| 188 | =$NOCH_3$ | 2 | 4-$CF_3$ | 4-$CF_3$ | Ethylsulfonate |
| 189 | =$NOCH_3$ | 2 | 4-$CF_3$ | 4-$CF_3$ | Ethylsulfonate |
| 190 | =$NOCH_2CH_3$ | 3 | 4-$CF_3$ | 4-$CF_3$ | Ethylsulfonate |
| 191 | =$NOCH_2CH_3$ | 2 | 4-$CF_3$ | 4-$CF_3$ | Ethylsulfonate |
| 192 | =$NOCH_2CH_2F$ | 3 | 4-$CF_3$ | 4-$CF_3$ | Ethylsulfonate |
| 193 | =$NOCH_2CH_2F$ | 2 | 4-$CF_3$ | 4-$CF_3$ | Ethylsulfonate |

TABLE 3

Inner Salts of Insecticidal N-(Phenylmethylazabicylo)benzhydryl Alcohols

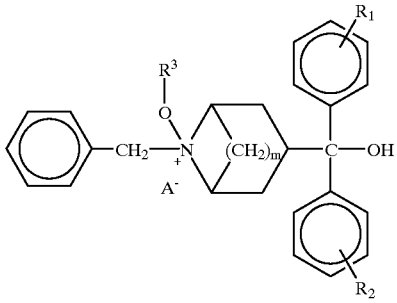

| No | X | m | $R^1$ | $R^2$ | $R^3$ | $A^-$ |
|---|---|---|---|---|---|---|
| 194 | $CO_2CH(CH_3)_2$ | 2 | 4-$CF_3$ | 4-$CF_3$ | $CH_3$ | Iodide |
| 195 | $CO_2CH(CH_3)_2$ | 2 | 4-$CF_3$ | 4-$CF_3$ | $CH_2CH_3COO^-$ | Inner Salt |
| 196 | $CO_2CH(CH_3)_2$ | 2 | 4-$CF_3$ | 4-$CF_3$ | $CH_2CH_2CO_2C_2H_5$ | Iodide |
| 197 | $CO_2CH(CH_3)_2$ | 2 | 4-$CF_3$ | 4-$CF_3$ | $CH_3$ | Bromide |
| 198 | $CO_2CH(CH_3)_2$ | 2 | 4-$CF_3$ | 4-$CF_3$ | $CH_2CH_3COO^-$ | Inner Salt |
| 199 | $CO_2CH(CH_3)_2$ | 2 | 4-$CF_3$ | 4-$CF_3$ | $CH_2CH_2CO_2C_2H_5$ | Bromide |
| 200 | $CO_2CH(CH_3)_2$ | 2 | 4-$OCF_3$ | 4-$OCF_3$ | $CH_3$ | Iodide |
| 201 | $CO_2CH(CH_3)_2$ | 2 | 4-$OCF_3$ | 4-$OCF_3$ | $CH_2CH_3COO^-$ | Inner Salt |
| 202 | $CO_2CH(CH_3)_2$ | 2 | 4-$OCF_3$ | 4-$OCF_3$ | $CH_2CH_2CO_2C_2H_5$ | Iodide |
| 203 | $CO_2CH(CH_3)_2$ | 2 | 4-$OCF_3$ | 4-$OCF_3$ | $CH_3$ | Bromide |
| 204 | $CO_2CH(CH_3)_2$ | 2 | 4-$OCF_3$ | 4-$OCF_3$ | $CH_2CH_3COO^-$ | Inner Salt |
| 205 | $CO_2CH(CH_3)_2$ | 2 | 4-$OCF_3$ | 4-$OCF_3$ | $CH_2CH_2CO_2C_2H_5$ | Bromide |
| 206 | $CO_2CH(CH_3)_2$ | 3 | 4-$CF_3$ | 4-$CF_3$ | $CH_3$ | Iodide |
| 207 | $CO_2CH(CH_3)_2$ | 3 | 4-$CF_3$ | 4-$CF_3$ | $CH_2CH_3COO^-$ | Inner Salt |
| 208 | $CO_2CH(CH_3)_2$ | 3 | 4-$CF_3$ | 4-$CF_3$ | $CH_2CH_2CO_2C_2H_5$ | Iodide |
| 209 | $CO_2CH(CH_3)_2$ | 3 | 4-$CF_3$ | 4-$CF_3$ | $CH_3$ | Bromide |
| 210 | $CO_2CH(CH_3)_2$ | 3 | 4-$CF_3$ | 4-$CF_3$ | $CH_2CH_3COO^-$ | Inner Salt |
| 211 | $CO_2CH(CH_3)_2$ | 3 | 4-$CF_3$ | 4-$CF_3$ | $CH_2CH_2CO_2C_2H_5$ | Bromide |
| 212 | $CO_2CH(CH_3)_2$ | 3 | 4-$OCF_3$ | 4-$OCF_3$ | $CH_3$ | Iodide |
| 213 | $CO_2CH(CH_3)_2$ | 3 | 4-$OCF_3$ | 4-$OCF_3$ | $CH_2CH_3COO^-$ | Inner Salt |

TABLE 3-continued

Inner Salts of Insecticidal N-(Phenylmethylazabicylo)benzhydryl Alcohols

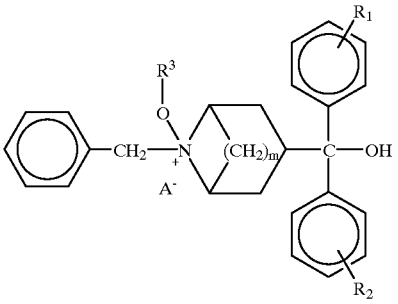

| No | X | m | $R^1$ | $R^2$ | $R^3$ | $A^-$ |
|---|---|---|---|---|---|---|
| 214 | $CO^2CH(CH_3)_2$ | 3 | 4-$OCF_3$ | 4-$OCF_3$ | $CH_2CH_2CO_2C_2H_5$ | Iodide |
| 215 | $CO_2CH(CH_3)_2$ | 3 | 4-$OCF_3$ | 4-$OCF_3$ | $CH_3$ | Bromide |
| 216 | $CO_2CH(CH_3)_2$ | 3 | 4-$OCF_3$ | 4-$OCF_3$ | $CH_2CH_3COO^-$ | Inner Salt |
| 217 | $CO_2CH(CH_3)_2$ | 3 | 4-$OCF_3$ | 4-$OCF_3$ | $CH_2CH_2CO_2C_2H_5$ | Bromide |
| 218 | $NHCO_2CH_3$ | 2 | 4-$CF_3$ | 4-$CF_3$ | $CH_3$ | Iodide |
| 219 | $NHCO_2CH_3$ | 2 | 4-$CF_3$ | 4-$CF_3$ | $CH_2CH_3COO^-$ | Inner Salt |
| 220 | $NHCO_2CH_3$ | 2 | 4-$CF_3$ | 4-$CF_3$ | $CH_2CH_2CO_2C_2H_5$ | Iodide |
| 221 | $NHCO_2CH_3$ | 2 | 4-$CF_3$ | 4-$CF_3$ | $CH_3$ | Bromide |
| 222 | $NHCO_2CH_3$ | 2 | 4-$CF_3$ | 4-$CF_3$ | $CH_2CH_3COO^-$ | Inner Salt |
| 223 | $NHCO_2CH_3$ | 2 | 4-$CF_3$ | 4-$CF_3$ | $CH_2CH_2CO_2C_2H_5$ | Bromide |
| 224 | $NHCO_2CH_3$ | 2 | 4-$OCF_3$ | 4-$OCF_3$ | $CH_3$ | Iodide |
| 225 | $NHCO_2CH_3$ | 2 | 4-$OCF_3$ | 4-$OCF_3$ | $CH_2CH_3COO^-$ | Inner Salt |
| 226 | $NHCO_2CH_3$ | 2 | 4-$OCF_3$ | 4-$OCF_3$ | $CH_2CH_2CO_2C_2H_5$ | Iodide |
| 227 | $NHCO_2CH_3$ | 2 | 4-$OCF_3$ | 4-$OCF_3$ | $CH_3$ | Bromide |
| 228 | $NHCO_2CH_3$ | 2 | 4-$OCF_3$ | 4-$OCF_3$ | $CH_2CH_3COO^-$ | Inner Salt |
| 229 | $NHCO_2CH_3$ | 2 | 4-$OCF_3$ | 4-$OCF_3$ | $CH_2CH_2CO_2C_2H_5$ | Bromide |
| 230 | $NHCO_2CH_3$ | 3 | 4-$CF_3$ | 4-$CF_3$ | $CH_3$ | Iodide |
| 231 | $NHCO_2CH_3$ | 3 | 4-$CF_3$ | 4-$CF_3$ | $CH_2CH_3COO^-$ | Inner Salt |
| 232 | $NHCO_2CH_3$ | 3 | 4-$CF_3$ | 4-$CF_3$ | $CH_2CH_2CO_2C_2H_5$ | Iodide |
| 233 | $NHCO_2CH_3$ | 3 | 4-$CF_3$ | 4-$CF_3$ | $CH_3$ | Bromide |
| 234 | $NHCO_2CH_3$ | 3 | 4-$CF_3$ | 4-$CF_3$ | $CH_2CH_3COO^-$ | Inner Salt |
| 235 | $NHCO_2CH_3$ | 3 | 4-$CF_3$ | 4-$CF_3$ | $CH_2CH_2CO_2C_2H_5$ | Bromide |
| 236 | $NHCO_2CH_3$ | 3 | 4-$OCF_3$ | 4-$OCF_3$ | $CH_3$ | Iodide |
| 237 | $NHCO_2CH_3$ | 3 | 4-$OCF_3$ | 4-$OCF_3$ | $CH_2CH_3COO^-$ | Inner Salt |
| 238 | $NHCO_2CH_3$ | 3 | 4-$OCF_3$ | 4-$OCF_3$ | $CH_2CH_2CO_2C_2H_5$ | Iodide |
| 239 | $NHCO_2CH_3$ | 3 | 4-$OCF_3$ | 4-$OCF_3$ | $CH_3$ | Bromide |
| 240 | $NHCO_2CH_3$ | 3 | 4-$OCF_3$ | 4-$OCF_3$ | $CH_2CH_3COO^-$ | Inner Salt |
| 241 | $NHCO_2CH_3$ | 3 | 4-$OCF_3$ | 4-$OCF_3$ | | |
| 242 | $NHCO_2CH(CH_3)_2$ | 2 | 4-$CF_3$ | 4-$CF_3$ | $CH_3$ | Iodide |
| 243 | $NHCO_2CH(CH_3)_2$ | 2 | 4-$CF_3$ | 4-$CF_3$ | $CH_2CH_3COO^-$ | Inner Salt |
| 244 | $NHCO_2CH(CH_3)_2$ | 2 | 4-$CF_3$ | 4-$CF_3$ | $CH_2CH_2CO_2C_2H_5$ | Iodide |
| 245 | $NHCO_2CH(CH_3)_2$ | 2 | 4-$CF_3$ | 4-$CF_3$ | $CH_3$ | Bromide |
| 246 | $NHCO_2CH(CH_3)_2$ | 2 | 4-$CF_3$ | 4-$CF_3$ | $CH_2CH_3COO^-$ | Inner Salt |
| 247 | $NHCO_2CH(CH_3)_2$ | 2 | 4-$CF_3$ | 4-$CF_3$ | $CH_2CH_2CO_2C_2H_5$ | Bromide |
| 248 | $NHCO_2CH(CH_3)_2$ | 2 | 4-$OCF_3$ | 4-$OCF_3$ | $CH_3$ | Iodide |
| 249 | $NHCO_2CH(CH_3)_2$ | 2 | 4-$OCF_3$ | 4-$OCF_3$ | $CH_2CH_3COO^-$ | Inner Salt |
| 250 | $NHCO_2CH(CH_3)_2$ | 2 | 4-$OCF_3$ | 4-$OCF_3$ | $CH_2CH_2CO_2C_2H_5$ | Iodide |
| 251 | $NHCO_2CH(CH_3)_2$ | 2 | 4-$OCF_3$ | 4-$OCF_3$ | $CH_3$ | Bromide |
| 252 | $NHCO_2CH(CH_3)_2$ | 2 | 4-$OCF_3$ | 4-$OCF_3$ | $CH_2CH_3COO^-$ | Inner Salt |
| 253 | $NHCO_2CH(CH_3)_2$ | 2 | 4-$OCF_3$ | 4-$OCF_3$ | $CH_2CH_2CO_2C_2H_5$ | Bromide |
| 254 | $NHCO_2CH(CH_3)_2$ | 3 | 4-$CF_3$ | 4-$CF_3$ | $CH_3$ | Iodide |
| 255 | $NHCO_2CH(CH_3)_2$ | 3 | 4-$CF_3$ | 4-$CF_3$ | $CH_2CH_3COO^-$ | Inner Salt |
| 256 | $NHCO_2CH(CH_3)_2$ | 3 | 4-$CF_3$ | 4-$CF_3$ | $CH_2CH_2CO_2C_2H_5$ | Iodide |
| 257 | $NHCO_2CH(CH_3)_2$ | 3 | 4-$CF_3$ | 4-$CF_3$ | $CH_3$ | Bromide |
| 258 | $NHCO_2CH(CH_3)_2$ | 3 | 4-$CF_3$ | 4-$CF_3$ | $CH_2CH_3COO^-$ | Inner Salt |
| 259 | $NHCO_2CH(CH_3)_2$ | 3 | 4-$CF_3$ | 4-$CF_3$ | $CH_2CH_2CO_2C_2H_5$ | Bromide |
| 260 | $NHCO_2CH(CH_3)_2$ | 3 | 4-$OCF_3$ | 4-$OCF_3$ | $CH_3$ | Iodide |
| 261 | $NHCO_2CH(CH_3)_2$ | 3 | 4-$OCF_3$ | 4-$OCF_3$ | $CH_2CH_3COO^-$ | Inner Salt |
| 262 | $NHCO_2CH(CH_3)_2$ | 3 | 4-$OCF_3$ | 4-$OCF_3$ | $CH_2CH_2CO_2C_2H_5$ | Iodide |
| 263 | $NHCO_2CH(CH_3)_2$ | 3 | 4-$OCF_3$ | 4-$OCF_3$ | $CH_3$ | Bromide |
| 264 | $NHCO_2CH(CH_3)_2$ | 3 | 4-$OCF_3$ | 4-$OCF_3$ | $CH_2CH_3COO^-$ | Inner Salt |
| 265 | $NHCO_2CH(CH_3)_2$ | 3 | 4-$OCF_3$ | 4-$OCF_3$ | $CH_2CH_2CO_2C_2H_5$ | Bromide |
| 266 | 2-methyltetrazol-5- | 2 | 4-$CF_3$ | 4-$CF_3$ | $CH_3$ | Iodide |
| 267 | 2-methyltetrazol-5- | 2 | 4-$CF_3$ | 4-$CF_3$ | $CH_2CH_3COO^-$ | Inner Salt |
| 268 | 2-methyltetrazol-5- | 2 | 4-$CF_3$ | 4-$CF_3$ | $CH_2CH_2CO_2C_2H_5$ | Iodide |
| 269 | 2-methyltetrazol-5- | 2 | 4-$CF_3$ | 4-$CF_3$ | $CH_3$ | Bromide |
| 270 | 2-methyltetrazol-5- | 2 | 4-$CF_3$ | 4-$CF_3$ | $CH_2CH_3COO^-$ | Inner Salt |
| 271 | 2-methyltetrazol-5- | 2 | 4-$CF_3$ | 4-$CF_3$ | $CH_2CH_2CO_2C_2H_5$ | Bromide |

TABLE 3-continued

Inner Salts of Insecticidal N-(Phenylmethylazabicylo)benzhydryl Alcohols

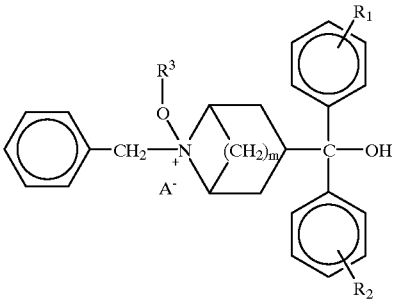

| No | X | m | $R^1$ | $R^2$ | $R^3$ | $A^-$ |
|---|---|---|---|---|---|---|
| 272 | 2-methyltetrazol-5- | 2 | 4-$OCF^3$ | 4-$OCF_3$ | $CH_3$ | Iodide |
| 273 | 2-methyltetrazol-5- | 2 | 4-$OCF_3$ | 4-$OCF_3$ | $CH_2CH_3COO^-$ | Inner Salt |
| 274 | 2-methyltetrazol-5- | 2 | 4-$OCF_3$ | 4-$OCF_3$ | $CH_2CH_2CO_2C_2H_5$ | Iodide |
| 275 | 2-methyltetrazol-5- | 2 | 4-$OCF_3$ | 4-$OCF_3$ | $CH_3$ | Bromide |
| 276 | 2-methyltetrazol-5- | 2 | 4-$OCF_3$ | 4-$OCF_3$ | $CH_2CH_3COO^-$ | Inner Salt |
| 277 | 2-methyltetrazol-5- | 2 | 4-$OCF_3$ | 4-$OCF_3$ | $CH_2CH_2CO_2C_2H_5$ | Bromide |
| 278 | 2-methyltetrazol-5- | 3 | 4-$CF_3$ | 4-$CF_3$ | $CH_3$ | Iodide |
| 279 | 2-methyltetrazol-5- | 3 | 4-$CF_3$ | 4-$CF_3$ | $CH_2CH_3COO^-$ | Inner Salt |
| 280 | 2-methyltetrazol-5- | 3 | 4-$CF_3$ | 4-$CF_3$ | $CH_2CH_2CO_2C_2H_5$ | Iodide |
| 281 | 2-methyltetrazol-5- | 3 | 4-$CF_3$ | 4-$CF_3$ | $CH_3$ | Bromide |
| 282 | 2-methyltetrazol-5- | 3 | 4-$CF_3$ | 4-$CF_3$ | $CH_2CH_3COO^-$ | Inner Salt |
| 283 | 2-methyltetrazol-5- | 3 | 4-$CF_3$ | 4-$CF_3$ | $CH_2CH_2CO_2C_2H_5$ | Bromide |
| 284 | 2-methyltetrazol-5- | 3 | 4-$OCF_3$ | 4-$OCF_3$ | $CH_3$ | Iodide |
| 285 | 2-methyltetrazol-5- | 3 | 4-$OCF_3$ | 4-$OCF_3$ | $CH_2CH_3COO^-$ | Inner Salt |
| 286 | 2-methyltetrazol-5- | 3 | 4-$OCF_3$ | 4-$OCF_3$ | $CH_2CH_2CO_2C_2H_5$ | Iodide |
| 287 | 2-methyltetrazol-5- | 3 | 4-$OCF_3$ | 4-$OCF_3$ | $CH_3$ | Bromide |
| 288 | 2-methyltetrazol-5- | 3 | 4-$OCF_3$ | 4-$OCF_3$ | $CH_2CH_3COO^-$ | Inner Salt |
| 289 | 2-methyltetrazol-5- | 3 | 4-$OCF_3$ | 4-$OCF_3$ | $CH_2CH_2CO_2C_2H_5$ | Bromide |
| 290 | 2-ethyltetrazol-5-yl | 2 | 4-$CF_3$ | 4-$CF_3$ | $CH_3$ | Iodide |
| 291 | 2-ethyltetrazol-5-yl | 2 | 4-$CF_3$ | 4-$CF_3$ | $CH_2CH_3COO^-$ | Inner Salt |
| 292 | 2-ethyltetrazol-5-yl | 2 | 4-$CF_3$ | 4-$CF_3$ | $CH_2CH_2CO_2C_2H_5$ | Iodide |
| 293 | 2-ethyltetrazol-5-yl | 2 | 4-$CF_3$ | 4-$CF_3$ | $CH_3$ | Bromide |
| 294 | 2-ethyltetrazol-5-yl | 2 | 4-$CF_3$ | 4-$CF_3$ | $CH_2CH_3COO^-$ | Inner Salt |
| 295 | 2-ethyltetrazol-5-yl | 2 | 4-$CF_3$ | 4-$CF_3$ | $CH_2CH_2CO_2C_2H_5$ | Bromide |
| 296 | 2-ethyltetrazol-5-yl | 2 | 4-$OCF_3$ | 4-$OCF_3$ | $CH_3$ | Iodide |
| 297 | 2-ethyltetrazol-5-yl | 2 | 4-$OCF_3$ | 4-$OCF_3$ | $CH_2CH_3COO^-$ | Inner Salt |
| 298 | 2-ethyltetrazol-5-yl | 2 | 4-$OCF_3$ | 4-$OCF_3$ | $CH_2CH_2CO_2C_2H_5$ | Iodide |
| 299 | 2-ethyltetrazol-5-yl | 2 | 4-$OCF_3$ | 4-$OCF_3$ | $CH_3$ | Bromide |
| 300 | 2-ethyltetrazol-5-yl | 2 | 4-$OCF_3$ | 4-$OCF_3$ | $CH_2CH_3COO^-$ | Inner Salt |
| 301 | 2-ethyltetrazol-5-yl | 2 | 4-$OCF_3$ | 4-$OCF_3$ | $CH_2CH_2CO_2C_2H_5$ | Bromide |
| 302 | 2-ethyltetrazol-5-yl | 3 | 4-$CF_3$ | 4-$CF_3$ | $CH_3$ | Iodide |
| 303 | 2-ethyltetrazol-5-yl | 3 | 4-$CF_3$ | 4-$CF_3$ | $CH_2CH_3COO^-$ | Inner Salt |
| 304 | 2-ethyltetrazol-5-yl | 3 | 4-$CF_3$ | 4-$CF_3$ | $CH_2CH_2CO_2C_2H_5$ | Iodide |
| 305 | 2-ethyltetrazol-5-yl | 3 | 4-$CF_3$ | 4-$CF_3$ | $CH_3$ | Bromide |
| 306 | 2-ethyltetrazol-5-yl | 3 | 4-$CF_3$ | 4-$CF_3$ | $CH_2CH_3COO^-$ | Inner Salt |
| 307 | 2-ethyltetrazol-5-yl | 3 | 4-$CF_3$ | 4-$CF_3$ | $CH_2CH_2CO_2C_2H_5$ | Bromide |
| 308 | 2-ethyltetrazol-5-yl | 3 | 4-$OCF_3$ | 4-$OCF_3$ | $CH_3$ | Iodide |
| 309 | 2-ethyltetrazol-5-yl | 3 | 4-$OCF_3$ | 4-$OCF_3$ | $CH_2CH_3COO^-$ | Inner Salt |
| 310 | 2-ethyltetrazol-5-yl | 3 | 4-$OCF_3$ | 4-$OCF_3$ | $CH_2CH_2CO_2C_2H_5$ | Iodide |
| 311 | 2-ethyltetrazol-5-yl | 3 | 4-$OCF_3$ | 4-$OCF_3$ | $CH_3$ | Bromide |
| 312 | 2-ethyltetrazol-5-yl | 3 | 4-$OCF_3$ | 4-$OCF_3$ | $CH_2CH_3COO^-$ | Inner Salt |
| 313 | 2-ethyltetrazol-5-yl | 3 | 4-$OCF_3$ | 4-$OCF_3$ | $CH_2CH_2CO_2C_2H_5$ | Bromide |
| 314 | pyrid-2-yll | 2 | 4-$CF_3$ | 4-$CF_3$ | $CH_3$ | Iodide |
| 315 | pyrid-2-yl | 2 | 4-$CF_3$ | 4-$CF_3$ | $CH_2CH_3COO^-$ | Inner Salt |
| 316 | pyrid-2-yl | 2 | 4-$CF_3$ | 4-$CF_3$ | $CH_2CH_2CO_2C_2H_5$ | Iodide |
| 317 | pyrid-2-yl | 2 | 4-$CF_3$ | 4-$CF_3$ | $CH_3$ | Bromide |
| 318 | pyrid-2-yl | 2 | 4-$CF_3$ | 4-$CF_3$ | $CH_2CH_3COO^-$ | Inner Salt |
| 319 | pyrid-2-yl | 2 | 4-$CF_3$ | 4-$CF_3$ | $CH_2CH_2CO_2C_2H_5$ | Bromide |
| 320 | pyrid-2-yl | 2 | 4-$OCF_3$ | 4-$OCF_3$ | $CH_3$ | Iodide |
| 321 | pyrid-2-yl | 2 | 4-$OCF_3$ | 4-$OCF_3$ | $CH_2CH_3COO^-$ | Inner Salt |
| 322 | pyrid-2-yl | 2 | 4-$OCF_3$ | 4-$OCF_3$ | $CH_2CH_2CO_2C_2H_5$ | Iodide |
| 323 | pyrid-2-yl | 2 | 4-$OCF_3$ | 4-$OCF_3$ | $CH_3$ | Bromide |
| 324 | pyrid-2-yl | 2 | 4-$OCF_3$ | 4-$OCF_3$ | $CH_2CH_3COO^-$ | Inner Salt |
| 325 | pyrid-2-yl | 2 | 4-$OCF_3$ | 4-$OCF_3$ | $CH_2CH_2CO_2C_2H_5$ | Bromide |
| 326 | pyrid-2-yll | 3 | 4-$CF_3$ | 4-$CF_3$ | $CH_3$ | Iodide |
| 327 | pyrid-2-yl | 3 | 4-$CF_3$ | 4-$CF_3$ | $CH_2CH_3COO^-$ | Inner Salt |
| 328 | pyrid-2-yl | 3 | 4-$CF_3$ | 4-$CF_3$ | $CH_2CH_2CO_2C_2H_5$ | Iodide |
| 329 | pyrid-2-yl | 3 | 4-$CF_3$ | 4-$CF_3$ | $CH_3$ | Bromide |

TABLE 3-continued

Inner Salts of Insecticidal N-(Phenylmethylazabicylo)benzhydryl Alcohols

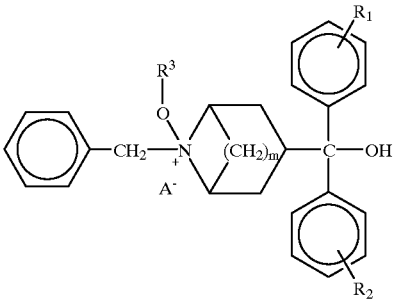

| No | X | m | $R^1$ | $R^2$ | $R^3$ | $A^-$ |
|---|---|---|---|---|---|---|
| 330 | pyrid-2-yl | 3 | 4-$CF^3$ | 4-$CF_3$ | $CH_2CH_3COO^-$ | Inner Salt |
| 331 | pyrid-2-yl | 3 | 4-$CF_3$ | 4-$CF_3$ | $CH_2CH_2CO_2C_2H_5$ | Bromide |
| 332 | pyrid-2-yll | 3 | 4-$OCF_3$ | 4-$OCF_3$ | $CH_3$ | Iodide |
| 333 | pyrid-2-yl | 3 | 4-$OCF_3$ | 4-$OCF_3$ | $CH_2CH_3COO^-$ | Inner Salt |
| 334 | pyrid-2-yl | 3 | 4-$OCF_3$ | 4-$OCF_3$ | $CH_2CH_2CO_2C_2H_5$ | Iodide |
| 335 | pyrid-2-yl | 3 | 4-$OCF_3$ | 4-$OCF_3$ | $CH_3$ | Bromide |
| 336 | pyrid-2-yl | 3 | 4-$OCF_3$ | 4-$OCF_3$ | $CH_2CH_3COO^-$ | Inner Salt |
| 337 | pyrid-2-yl | 3 | 4-$OCF_3$ | 4-$OCF_3$ | $CH_2CH_2CO_2C_2H_5$ | Bromide |
| 338 | pyrid-2-yloxy | 2 | 4-$CF_3$ | 4-$CF_3$ | $CH_3$ | Iodide |
| 339 | pyrid-2-yloxy | 2 | 4-$CF_3$ | 4-$CF_3$ | $CH_2CH_3COO^-$ | Inner Salt |
| 340 | pyrid-2-yloxy | 2 | 4-$CF_3$ | 4-$CF_3$ | $CH_2CH_2CO_2C_2H_5$ | Iodide |
| 341 | pyrid-2-ylxoy | 2 | 4-$CF_3$ | 4-$CF_3$ | $CH_3$ | Bromide |
| 342 | pyrid-2-yloxy | 2 | 4-$CF_3$ | 4-$CF_3$ | $CH_2CH_3COO^-$ | Inner Salt |
| 343 | pyrid-2-yloxy | 2 | 4-$CF_3$ | 4-$CF_3$ | $CH_2CH_2CO_2C_2H_5$ | Bromide |
| 344 | pyrid-2-yloxy | 2 | 4-$OCF_3$ | 4-$OCF_3$ | $CH_3$ | Iodide |
| 345 | pyrid-2-yloxy | 2 | 4-$OCF_3$ | 4-$OCF_3$ | $CH_2CH_3COO^-$ | Inner Salt |
| 346 | pyrid-2-yloxy | 2 | 4-$OCF_3$ | 4-$OCF_3$ | $CH_2CH_2CO_2C_2H_5$ | Iodide |
| 347 | pyrid-2-yloxy | 2 | 4-$OCF_3$ | 4-$OCF_3$ | $CH_3$ | Bromide |
| 348 | pyrid-2-yloxy | 2 | 4-$OCF_3$ | 4-$OCF_3$ | $CH_2CH_3COO^-$ | Inner Salt |
| 349 | pyrid-2-yloxy | 2 | 4-$OCF_3$ | 4-$OCF_3$ | $CH_2CH_2CO_2C_2H_5$ | Bromide |
| 350 | pyrid-2-yloxy | 3 | 4-$CF_3$ | 4-$CF_3$ | $CH_3$ | Iodide |
| 351 | pyrid-2-yloxy | 3 | 4-$CF_3$ | 4-$CF_3$ | $CH_2CH_3COO^-$ | Inner Salt |
| 352 | pyrid-2-yloxy | 3 | 4-$CF_3$ | 4-$CF_3$ | $CH_2CH_2CO_2C_2H_5$ | Iodide |
| 353 | pyrid-2-yloxy | 3 | 4-$CF_3$ | 4-$CF_3$ | $CH_3$ | Bromide |
| 354 | pyrid-2-yloxy | 3 | 4-$CF_3$ | 4-$CF_3$ | $CH_2CH_3COO^-$ | Inner Salt |
| 355 | pyrid-2-yloxy | 3 | 4-$CF_3$ | 4-$CF_3$ | $CH_2CH_2CO_2C_2H_5$ | Bromide |
| 356 | pyrid-2-yloxy | 3 | 4-$OCF_3$ | 4-$OCF_3$ | $CH_3$ | Iodide |
| 357 | pyrid-2-yloxy | 3 | 4-$OCF_3$ | 4-$OCF_3$ | $CH_2CH_3COO^-$ | Inner Salt |
| 358 | pyrid-2-yloxy | 3 | 4-$OCF_3$ | 4-$OCF_3$ | $CH_2CH_2CO_2C_2H_5$ | Iodide |
| 359 | pyrid-2-yloxy | 3 | 4-$OCF_3$ | 4-$OCF_3$ | $CH_3$ | Bromide |
| 360 | pyrid-2-yloxy | 3 | 4-$OCF_3$ | 4-$OCF_3$ | $CH_2CH_3COO^-$ | Inner Salt |
| 361 | pyrid-2-yloxy | 3 | 4-$OCF_3$ | 4-$OCF_3$ | $CH_2CH_2CO_2C_2H_5$ | Bromide |
| 362 | cyclopropyloxy | 2 | 4-$CF_3$ | 4-$CF_3$ | $CH_3$ | Iodide |
| 363 | cyclopropyloxy | 2 | 4-$CF_3$ | 4-$CF_3$ | $CH_2CH_3COO^-$ | Inner Salt |
| 364 | cyclopropyloxy | 2 | 4-$CF_3$ | 4-$CF_3$ | $CH_2CH_2CO_2C_2H_5$ | Iodide |
| 365 | cyclopropyloxy | 2 | 4-$CF_3$ | 4-$CF_3$ | $CH_3$ | Bromide |
| 366 | cyclopropyloxy | 2 | 4-$CF_3$ | 4-$CF_3$ | $CH_2CH_3COO^-$ | Inner Salt |
| 367 | cyclopropyloxy | 2 | 4-$CF_3$ | 4-$CF_3$ | $CH_2CH_2CO_2C_2H_5$ | Bromide |
| 368 | cyclopropyloxy | 2 | 4-$OCF_3$ | 4-$OCF_3$ | $CH_3$ | Iodide |
| 369 | cyclopropyloxy | 2 | 4-$OCF_3$ | 4-$OCF_3$ | $CH_2CH_3COO^-$ | Inner Salt |
| 370 | cyclopropyloxy | 2 | 4-$OCF_3$ | 4-$OCF_3$ | $CH_2CH_2CO_2C_2H_5$ | Iodide |
| 371 | cyclopropyloxy | 2 | 4-$OCF_3$ | 4-$OCF_3$ | $CH_3$ | Bromide |
| 372 | cyclopropyloxy | 2 | 4-$OCF_3$ | 4-$OCF_3$ | $CH_2CH_3COO^-$ | Inner Salt |
| 373 | cyclopropyloxy | 2 | 4-$OCF_3$ | 4-$OCF_3$ | $CH_2CH_2CO_2C_2H_5$ | Bromide |
| 374 | cyclopropyloxy | 3 | 4-$CF_3$ | 4-$CF_3$ | $CH_3$ | Iodide |
| 375 | cyclopropyloxy | 3 | 4-$CF_3$ | 4-$CF_3$ | $CH_2CH_3COO^-$ | Inner Salt |
| 376 | cyclopropyloxy | 3 | 4-$CF_3$ | 4-$CF_3$ | $CH_2CH_2CO_2C_2H_5$ | Iodide |
| 377 | cyclopropyloxy | 3 | 4-$CF_3$ | 4-$CF_3$ | $CH_3$ | Bromide |
| 378 | cyclopropyloxy | 3 | 4-$CF_3$ | 4-$CF_3$ | $CH_2CH_3COO^-$ | Inner Salt |
| 379 | cyclopropyloxy | 3 | 4-$CF_3$ | 4-$CF_3$ | $CH_2CH_2CO_2C_2H_5$ | Bromide |
| 380 | cyclopropyloxy | 3 | 4-$OCF_3$ | 4-$OCF_3$ | $CH_3$ | Iodide |
| 381 | cyclopropyloxy | 3 | 4-$OCF_3$ | 4-$OCF_3$ | $CH_2CH_3COO^-$ | Inner Salt |
| 382 | cyclopropyloxy | 3 | 4-$OCF_3$ | 4-$OCF_3$ | $CH_2CH_2CO_2C_2H_5$ | Iodide |
| 383 | cyclopropyloxy | 3 | 4-$OCF_3$ | 4-$OCF_3$ | $CH_3$ | Bromide |
| 384 | cyclopropyloxy | 3 | 4-$OCF_3$ | 4-$OCF_3$ | $CH_2CH_3COO^-$ | Inner Salt |
| 385 | cyclopropyloxy | 3 | 4-$OCF_3$ | 4-$OCF_3$ | $CH_2CH_2CO_2C_2H_5$ | Bromide |

TABLE 3-continued

Inner Salts of Insecticidal N-(Phenylmethylazabicylo)benzhydryl Alcohols

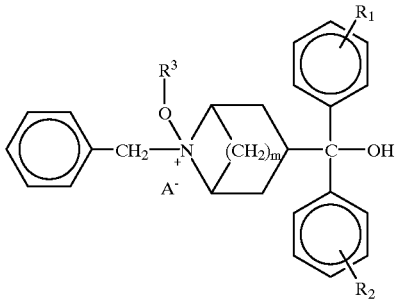

| No | X | m | $R^1$ | $R^2$ | $R^3$ | $A^-$ |
|---|---|---|---|---|---|---|
| 386 | $OC^3H_7$ | 3 | 4-$OCF_3$ | 4-$OCF_3$ | $CH_2CH_3COO^-$ | Inner Salt |
| 387 | =N—O—$CH_3$ | 3 | 4-$OCF_3$ | 4-$OCF_3$ | $CH_2CH_2CO_2C_2H_2$ | Bromide |
| 388 | =N—O—$CH_3$ | 3 | 4-$OCF_3$ | 4-$OCF_3$ | $CH_2CH_2COO$ | Inner Salt |

TABLE 4

Salts of Insecticidal N-(Phenylmethylazabicyclo)benshydryl Alcohols

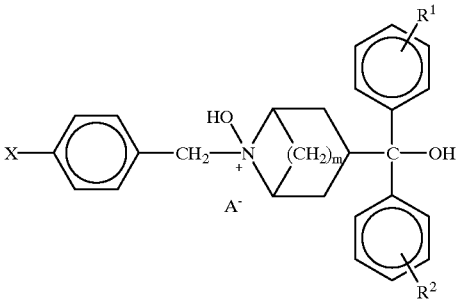

| N | X | m | $R^1$ | $R^2$ | $A^-$ |
|---|---|---|---|---|---|
| 389 | 2-ethyltetrazol-5-yl | 3 | 4-$CF_3$ | 4-$CF_3$ | Ethylsulfonate |
| 390 | 2-ethyltetrazol-5-yl | 3 | 4-$CF_3$ | 4-$CF_3$ | Ethylsulfonate |
| 391 | 2-ethyltetrazol-5-yl | 3 | 4-$CF_3$ | 4-$CF_3$ | Hydrochloride |
| 392 | 2-ethyltetrazol-5-yl | 3 | 4-$OCF_3$ | 4-$OCF_3$ | Salicylate |
| 393 | 2-ethyltetrazol-5-yl | 3 | 4-$OCF_3$ | 4-$OCF_3$ | Ethylsulfonate |
| 394 | 2-ethyltetrazol-5-yl | 3 | 4-$OCF_3$ | 4-$OCF_3$ | Hydrochloride |
| 395 | 2-ethyltetrazol-5-yl | 2 | 4-$CF_3$ | 4-$CF_3$ | Salicylate |
| 396 | 2-ethyltetrazol-5-yl | 2 | 4-$CF_3$ | 4-$CF_3$ | Ethylsulfonate |
| 397 | 2-ethyltetrazol-5-yl | 2 | 4-$CF_3$ | 4-$CF_3$ | Hydrochloride |
| 398 | 2-ethyltetrazol-5-yl | 2 | 4-$OCF_3$ | 4-$OCF_3$ | Salicylate |
| 399 | 2-ethyltetrazol-5-yl | 2 | 4-$OCF_3$ | 4-$OCF_3$ | Ethylsulfonate |
| 400 | 2-ethyltetrazol-5-yl | 2 | 4-$OCF_3$ | 4-$OCF_3$ | Hydrochloride |
| 401 | 2-methyltetrazol-5-yl | 3 | 4-$OCF_3$ | 4-$OCF_3$ | Salicylate |
| 402 | 2-methyltetrazol-5-yl | 2 | 4-$OCF_3$ | 4-$OCF_3$ | Ethylsulfonate |
| 403 | 2-methyltetrazol-5-yl | 3 | 4-$CF_3$ | 4-$CF_3$ | Ethylsulfonate |
| 404 | 2-methyltetrazol-5-yl | 2 | 4-$CF_3$ | 4-$CF_3$ | Ethylsulfonate |
| 405 | pyrid-2-yloxy | 3 | 4-$CF_3$ | 4-$CF_3$ | Ethylsulfonate |
| 406 | pyrid-2-yloxy | 3 | 4-$OCF_3$ | 4-$OCF_3$ | Ethylsulfonate |
| 407 | pyrid-2-yloxy | 2 | 4-$CF_3$ | 4-$CF_3$ | Ethylsulfonate |
| 408 | pyrid-2-yloxy | 2 | 4-$OCF_3$ | 4-$OCF_3$ | Ethylsulfonate |
| 409 | $NHCO_2CH_3$ | 3 | 4-$CF_3$ | 4-$CF_3$ | Ethylsulfonate |
| 410 | $NHCO_2CH_3$ | 3 | 4-$OCF_3$ | 4-$OCF_3$ | Ethylsulfonate |
| 411 | $NHCO_2CH_3$ | 2 | 4-$CF_3$ | 4-$CF_3$ | Ethylsulfonate |
| 412 | $NHCO_2CH_3$ | 2 | 4-$OCF_3$ | 4-$OCF_3$ | Ethylsulfonate |
| 413 | $CO_2CH(CH_3)_2$ | 3 | 4-$CF_3$ | 4-$CF_3$ | Ethylsulfonate |
| 414 | $CO_2CH(CH_30_2$ | 3 | 4-$OCF_3$ | 4-$OCF_3$ | Ethylsulfonate |
| 415 | $CO_2CH(CH_3)_2$ | 2 | 4-$CF_3$ | 4-$CF_3$ | Ethylsulfonate |
| 416 | $CO_2CH(CH_30_2$ | 2 | 4-$OCF_3$ | 4-$OCF_3$ | Ethylsulfonate |
| 417 | =N—O—$CH_3$ | 3 | 4-$CF_3$ | 4-$CF_3$ | Ethylsulfonate |

TABLE 4-continued

Salts of Insecticidal N-(Phenylmethylazabicyclo)benshydryl Alcohols

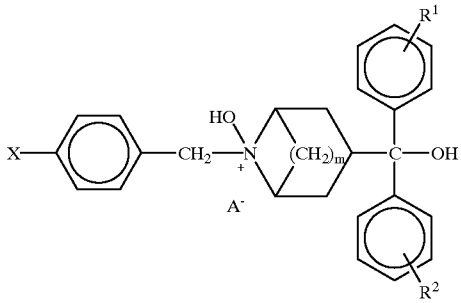

| N | X | m | $R^1$ | $R^2$ | $A^-$ |
|---|---|---|---|---|---|
| 418 | =N—O—$CH^3$ | 3 | 4-$OCF_3$ | 4-$OCF_3$ | Ethylsulfonate |
| 419 | =N—O—$CH_3$ | 2 | 4-$CF_3$ | 4-$CF_3$ | Ethylsulfonate |
| 420 | =N—O—$CH_3$ | 2 | 4-$OCF_3$ | 4-$OCF_3$ | Ethylsulfonate |
| 421 | =N—O—$CH_2CH_3$ | 3 | 4-$CF_3$ | 4-$CF_3$ | Ethylsulfonate |
| 422 | =N—O—$CH_2CH_3$ | 3 | 4-$OCF_3$ | 4-$OCF_3$ | Ethylsulfonate |
| 423 | =N—O—$CH_2CH_3$ | 2 | 4-$CF_3$ | 4-$CF_3$ | Ethylsulfonate |
| 424 | =N—O—$CH_2CH_3$ | 2 | 4-$OCF_3$ | 4-$OCF_3$ | Ethylsulfonate |
| 425 | =N—O—$CH_2CH_2F$ | 3 | 4-$CF_3$ | 4-$CF_3$ | Ethylsulfonate |
| 426 | =N—O—$CH_2CH_2F$ | 3 | 4-$OCF_3$ | 4-$OCF_3$ | Ethylsulfonate |
| 427 | =N—O—$CH_2CH_2F$ | 2 | 4-$CF_3$ | 4-$CF_3$ | Ethylsulfonate |
| 428 | =N—O—$CH_2CH_2F$ | 2 | 4-$OCF_3$ | 4-$OCF_3$ | Ethylsulfonate |
| 429 | $OC_3H_7$ | 3 | 4-$CF_3$ | 4-$CF_3$ | Ethylsulfonate |

The compounds of this invention may be used to combat, control, or prevent infestations of insect pests such as Lepidoptera, Diptera, Homoptera, Coleoptera, and Diabrotica such as corn rootworms as well as other invertebrate pests such as Acarids. In general the compounds of the invention may be used to control insects and acarids found in agricultural crops, horticulture, and animal husbandry. They are also useful in forestry, storage and preservation of products of vegetable origin, and for controlling those insect and acarine pests associated with transmission of diseases of man and animals.

Examples of pest species some or all of which may be effectively controlled by the compounds of the invention include *Myzus persicae* (aphid), *Aphis gossypii* (aphid),

*Aedes aegypti* (mosquito), Anopheles species (mosquitoes), Culex species (mosquitoes), *Dysdercus faciatus* (capsid), *Musca domestica* (housefly), *Pieris brassicae* (white butterfly), *Plutella xylostella* (black diamond moth), *Phaedon cochleariae* (mustard beetle), Aonidiella species (scale insects), Trialeurodes species (white flies), *Bemisia tabaci* (white fly), *Blatella germanica* (cockroach), *Periplaneta americana* (cockroach), *Blatta orientalis* (cockroach), *Spodoptera littoralis* (cotton leafworm), *Heliothis virescens* (tobacco budworm, *Chortiocetes terminifera* (locust), Diabrotica species (rootworms), Asrotis species (cutworms), *Chilo partellus* (maize stem borer), *Nilaparvata lus'ens* (planthopper, *Nephotettix cincticeps* (leafhopper), *Panonychus ulmi* (European red mite), *Panonychus citri* (citrus red mite), *Tetranychus urticae* (two-spotted spider mite), *Tetranychus cinnabarinus* (carmine spider mite, *Phylocoptruta oleivora* (citrus rust mite), *Polyphagotarsonemus latus* (broad mite) and various Brevapalpus species (mites).

In accordance with the method for controlling such pests, the insecticides of this invention are normally formulated into compositions which include a pesticidally effective amount of the active ingredient of this invention in addition to suitable compatible and inert diluents, carriers, surfactants and the like. Such compositions are generally applied to the locus where control is desired, which may include the soil in which plants are or are to be grown or stored, to plants or animals themselves, or to other loci where control or prevention of infestation is required.

It will be appreciated by those skilled in the art that the formulations in which the compounds of the invention may suitably be applied include such formulations as dusts, wettable powders, granules, solutions, emulsions suspensions, and various concentrates such as solution concentrates or suspension concentrates, and also as controlled release compositions such as microencapsulated granules or suspensions. Such formulations are well known to those skilled in the art. It will also be appreciated by those skilled in the art that the compounds of the invention may be used alone as a single active ingredient of such formulations or in combination with other known pesticides, such as other insecticides, acaricides, fungicides, plant growth and development regulators, herbicides and combinations of such other active ingredients.

The examples set forth below further demonstrate the preparation and use of selected compounds of the invention for illustration purposes only and not by way of limitation on the scope and content of that which the inventors regard as their invention.

EXAMPLE 1

Synthesis of 9-phenylmethyl-α,α-bis(4-trifluoromethylphenyl)-9-azabicyclo[3.3.1.]nonane-3-methanol (Compound 1)

Step A: 3-cyano-9-phenylmethyl-9-azabicyclo[3.3.1]nonane as an intermediate.

To a stirred solution of 2.0 grams (0.009 mole) of 9-phenylmethyl-9-azabicyclo[3.3.1]nonane-3-one (prepared in the manner disclosed by Lowe et al., (J.Med. Chem., 1994 37, 2831–2840) in 55 ml of 1,1-dimethoxyethane was added 3.06 grams (0.016 mole) of tosylmethyl isocyanide. Upon completion of addition, the mixture was cooled to 0° C. and 1.17 ml (0.020 mole) of ethanol was added followed by 3.42 grams (0.031 mole) of potassium t-butoxide in four portions. Upon completion of addition, the reaction mixture was allowed to warm to ambient temperature and then heated to 50° C. where it stirred for five hours. After this time, the reaction mixture was allowed to cool to ambient temperature were it stirred for about 18 hours. The reaction mixture was analyzed by gas chromatography (GC), which indicated the reaction was incomplete. The above procedure was repeated and an additional 1.7 grams (0.007 mole) of 9-phenylmethyl-9-azabicyclo[3.3.1]nonane-3-one was added. The reaction mixture was heated to 55° C. where it stirred for two hours. After this time, the reaction mixture was again analyzed by GC, which indicated the reaction was incomplete. The reaction mixture was heated at about 50° C. for an additional three hours and then cooled to ambient temperature where it stirred for about 18 hours. The reaction mixture was poured into 150 ml of an aqueous saturated sodium chloride solution, and the resulting mixture was extracted with ethyl acetate. The organic layer was separated from the aqueous layer, dried with sodium sulfate, and filtered. The filtrate was concentrated under reduced pressure to yield 4.5 grams of crude product. The crude product was purified by column chromatography, yielding 0.41 grams of the above identified intermediate. The NMR spectrum was consistent with the proposed structure.

Step B: Ethyl N-(9-phenylmethyl-9-azabicyclo[3.3.1]nonane-3-yl)carboxylate as an intermediate.

In a 100 ml roundbottom flask, 250 ml of ethanol was saturated with hydrochloric gas for 40 minutes. After this time, 0.41 gram (0.002 mole) of 3-cyano-9-phenylmethyl-9-azabicyclo[3.3.1]nonane was taken up in 12 ml of the saturated ethanol. The solution was heated to reflux and 0.2 ml of water was added. Upon completion of addition, the reaction mixture was heated at reflux for about 18 hours. At the conclusion of this period, the ethanol was removed under reduced pressure and the hydrochloric gas was neutralized with an aqueous 5% sodium hydroxide solution. The resulting mixture was extracted with methylene chloride and washed with an aqueous saturated sodium chloride solution. The organic layer was separated from the aqueous layer, dried with sodium sulfate, and filtered. The filtrate was concentrated under reduced pressure to yield the crude product. The crude product was purified by column chromatography, yielding 0.3 gram of the above identified intermediate. The NMR spectrum was consistent with the proposed spectrum.

Step C: Compound 1

Under a nitrogen atmosphere, 0.42 gram (0.0174 mole) of turnings magnesium was taken up in 5.0 ml of anhydrous tetrahydrofuran. The resulting solution was heated to about 60° C. to effect dissolution. The tetrahydrofuran was removed via a syringe and the magnesium was dried at about 60° C. for five minutes. After this time, the magnesium was allowed to cool to ambient temperature and an additional 5.0 ml of tetrahydrofuran was added followed by 0.5 (0.0022 mole) of 1-trifluoromethyl-4-bromobenzene. To this solution was added an additional 2.0 ml of tetrahydrofuran and one small crystal of iodine. The resulting solution was heated until the iodine color disappeared. In an independent separatory funnel, 3.42 grams (0.0153 mole) of 1-trifluoromethyl-4-bromobenzene was taken up in 20 ml of tetrahydrofuran. To this solution was added a solution of 2.0 grams (0.007 mole) of ethyl N-(9-phenylmethyl-9-azabicyclo[3.3.1]nonane-3-yl)carboxylate in 28 ml of tetrahydrofuran. The resulting mixture was added dropwise to the iodine solution. Upon completion of addition, the reaction mixture was heated to 60° C. where it stirred for 2.5 hours. The reaction mixture was allowed to cool to ambient temperature where it stirred for about 18 hours. At the conclusion of this period, 50 ml of ammonium chloride was added, and the resulting mixture was extracted with two portions of ethyl acetate. The combined ethyl acetate extracts were dried with sodium sulfate and filtered. The filtrate was concentrated under reduced pressure, yielding 4.6 grams of crude product. The crude product was purified by column chromatography, yielding 2.3 grams of 9-phenylmethyl-α,α-bis(4-trifluoromethylphenyl)-9-azabicyclo[3.3.1.]nonane-3-methanol (Compound 1) as a yellow oil. The NMR spectrum was consistent with the proposed spectrum.

EXAMPLE 2

9-(4-propoxyphenyl)methyl-α,α-bis(4-trifluoromethylphenyl)-9-azabicyclo[3.3.1.]nonane-3-methanol (Compound 2)

Step A: 9-phenylmethyl-α,α-bis(4-trifluoromethylphenyl)-9-azabicyclo[3.3.1.]nonane-3-methanol hydrochloride salt as an intermediate.

A stirred solution of 2.3 grams (0.0043 mole) of 9-phenylmethyl-α,α-bis(4-trifluoromethylphenyl)-9-azabicyclo[3.3.1.]nonane-3-methanol in 30 ml of diethyl ether was cooled to 0° C. and 30 ml of a hydrochloric acid and diethyl ether mixture was added dropwise. Upon completion of addition, the reaction mixture was allowed to warm to ambient temperature and 100 ml of pentane was added. The solvent was removed under reduced pressure, yielding 2.5 grams of the above identified intermediate. The NMR spectrum was consistent with the proposed structure Step B: α,α-bis(4-trifluoromethylphenyl)-9-azabicyclo[3.3.1.]nonane-3-methanol as an intermediate.

Under a nitrogen atmosphere, a stirred solution of 2.49 grams (0.0044 mole) of 9-phenylmethyl-α,α-bis(4-trifluoromethylphenyl)-9-azabicyclo[3.3.1.]nonane-3-methanol hydrochloride salt in 40 ml of absolute methanol was treated with 0.75 grams of 10% palladium in carbon in 52 ml of absolute methanol. The reaction mixture was heated to 65° C. where it stirred for 1.5 hours. After this time, the reaction mixture was cooled to ambient temperature, filtered through diatomaceous earth, and the resulting filter cake was washed with 200 ml of methylene chloride. The filtrate was concentrated under reduced pressure, and the resulting residue was taken up in a 5% aqueous sodium hydroxide solution. The solution was extracted with three 100 ml portions of chloroform. The organic layer was separated from the aqueous layer and concentrated under reduce pressure, yielding 1.6 grams of the above identified intermediate structure, m.p. 172–179° C. The NMR spectrum was consistent with the proposed spectrum.

Step C: (Compound 2)

Under a nitrogen atmosphere, 1.3 grams (0.0029 mole) of α,α-bis(4-trifluoromethylphenyl)-9-azabicyclo[3.3.1.]nonane-3-methanol was taken up in 15 ml of dimethyl sulfoxide. To this solution was added a solution of 0.6 gram (0.0032 mole) of 4-propoxyphenylmethyl chloride in 6 ml of dimethyl sulfoxide. The resulting solution was stirred for five minutes and then 1.5 grams (0.0116 mole) of N,N-diisopropylethylamine was added via syringe. Upon completion of addition, the reaction mixture was stirred at ambient temperature for 20 hours. At the conclusion of this period, the reaction mixture was poured into a mixture consisting of 100 ml of an aqueous saturated sodium bicarbonate solution, 20 ml of an aqueous 10% sodium hydroxide solution, and 300 ml of ethyl acetate. The organic layer was separated, washed with one 100 ml portion of an aqueous saturated sodium chloride solution, dried with sodium sulfate, and filtered. The filtrate was concentrated under reduced pressure to yield a yellow oil. The yellow oil was taken up in ethyl acetate, and the resulting solution was filtered through a silica gel plug. The filtrate was concentrated under reduced pressure, yielding 1.4 grams of crude product. The crude product was purified by column chromatography, yielding 1.3 grams of Compound 2, m.p. 109–111° C. The NMR spectrum was consistent with the proposed structure.

EXAMPLE 3

9-(4-propoxyphenyl)methyl-α,α-bis(4-trifluoromethylphenyl)-9-azabicyclo[3.3.1.]nonane-3-methanol N-oxide (Compound 3)

A stirred solution of 0.8 gram (0.0014 mole) of 9-(4-propoxyphenyl)-methyl- α,α-bis(4-trifluoromethylphenyl)-9-azabicyclo[3.3.1.]nonane-3-methanol in 20 ml of chloroform was cooled to about 10° C. and 0.43 gram (0.0015 mole) of 60% 3-chloroperoxybenzoic acid was added. Upon completion of addition, the reaction mixture was allowed to warm to ambient temperature where it stirred for about 18 hours. After this time, an additional 150 ml of chloroform was added, and the resulting solution was washed with one 100 ml portion of a cold aqueous 5% sodium hydroxide solution. The organic layer was separated from the aqueous, dried with sodium sulfate, and filtered. The filtrate was concentrated under reduced pressure, yielding 0.69 gram of Compound 3, m.p. 179–184° C. The NMR spectrum was consistent with the proposed structure.

EXAMPLE 4

9-(4-propoxyphenyl)methyl-α,α-bis(4-trifluoromethylphenyl)-9-azabicyclo [3.3.1.]nonane-3-methanol hydrochloride (Compound 118)

To a stirred suspension of 0.65 gram (0.0011 mole) of 9-(4-propoxyphenyl)-methyl-α,α-bis(4-triluoromethylphenyl)-9-azabicyclo[3.3.1.]nonane-3-methanol in 10 ml of diethyl ether is added dropwise a solution of 2.2 ml (0.022 mole) of hydrochloric acid in 20 ml of diethyl ether. Upon completion of addition, the reaction mixture is stirred at ambient temperature for about 18 hours. After this time, the diethyl ether is removed under reduced pressure to yield a residue. This residue when triturated with pentane and dried under reduced pressure, will yield Compound 118.

EXAMPLE 5

Ethanesulfonate salt of 9-(4-propoxyphenyl)methyl-α,α-bis(4-trifluoromethylphenyl)-9-azabicyclo [3.3.1.]nonane-3-methanol (Compound 119)

To a stirred suspension of 0.65 gram (0.0011 mole) of 9-(4-propoxyphenyl)-methyl-α,α-bis(4-trifluoromethylphenyl)-9-azabicyclo[3.3.1.]nonane-3-methanol in 10 ml of diethyl ether is added dropwise a solution of 0.18 ml (0.022 mole) of ethanesulfonic acid in 20 ml of diethyl ether. Upon completion of addition, the reaction mixture is stirred at ambient temperature for five hours. After this time, the diethyl ether is removed under reduced pressure to yield a brown oil. The oil is then up in 20 ml of methylene chloride, and the resulting solution is washed with one five ml portion of water. The organic layer is separated from the aqueous layer, dried with sodium sulfate, and filtered. The filtrate when concentrated under reduced pressure, will yield the Compound 119.

EXAMPLE 6

9-(4-propoxyphenyl)methyl-α,α-bis(4-trifluoromethylphenyl)-9-(2-carboxyethoxy)-9-azabicyclo[3.3.1.]nonane-3-methanol N-oxide (Compound 386)

Under a nitrogen atmosphere, a solution of 0.61 gram (0.001 mole) of 9-(4-propoxyphenyl)methyl- α,α-bis(4-trifluoromethylphenyl)-9-azabicyclo[3.3.1.]nonane-3-methanol N-oxide, 0.15 gram (0.001 mole) of 3-bromopropionic acid, and a 1:1 mixture of acetonitrile and chloroform is stirred at ambient temperature for about 48 hours. The reaction mixture is then filtered. The filtrate when concentrated under reduced pressure, will then yield Compound 386.

EXAMPLE 7

Ethanesulfonate salt of 9-(4-propoxyphenyl)methyl-α,α-bis(4-trifluoromethylphenyl)-9azabicyclo[3.3.1] nonane-3-methanol N-oxide (Compound 429)

Under a nitrogen atmosphere, to a stirred suspension of 0.61 gram (0.001 mole) of 9-(4-propoxyphenyl)methyl-α, α-bis(4-trifluoromethylphenyl)-9-azabicyclo[3.3.1.] nonane-3-methanol N-oxide in 1 ml of ethanol is added dropwise a solution of 0.22 gram (0.002 mole) of ethanesulfonic acid in 0.5 ml of ethanol. Upon completion of addition, the reaction mixture is stirred at ambient temperature for 12 hours. After this time, the reaction mixture is washed with one 15 ml portion of heptane. The resulting solid may the be separated from the aqueous layer, dried with sodium sulfate, and filtered. The filtrate, when concentrated under reduced pressure, will yield Compound 429.

EXAMPLE 8

Insecticidal activity against the tobacco budworm (*Heliothis virescens* [Fabricius])

Stock solutions of test chemical in dimethylsulfoxide were prepared for each rate of application. The rates of application, expressed as the negative log of the molar concentration, and the corresponding concentrations of the stock solution prepared for each rate are shown below:

| Stock Solution | Rate of Application |
|---|---|
| 50 micromolar | 4 |
| 5 | 5 |
| 0.5 | 6 |
| 0.05 | 7 |
| 0.005 | 8 |

One hundred microliters of each of the stock solutions was manually stirred into 50 ml of a molten (65–70° C.) wheat germ-based artificial diet. The 50 ml of molten diet containing the test chemical was poured evenly into twenty wells in the outer four rows of a twenty-five well, five row plastic tray. Each well in the tray was about 1 cm in depth, with an opening of 3 cm by 4 cm at the lip. Molten diet containing only dimethylsulfoxide at the levels used in the test chemical-treated diet was poured into the five wells in the third row of the tray. Each tray therefore contained one test chemical at a single rate of application, together with an untreated control. Single second instar tobacco budworm larvae were placed in each well. The larvae were selected at a stage of growth at which they uniformly weigh about 5 mg each. Upon completion of infestation, a sheet of clear plastic was heat-sealed over the top of the tray using a common household flat iron. The trays were held at 25° C. at 60% relative humidity for five days in a growth chamber. Lighting was set at 14 hours of light and 10 hours of darkness. After the 5-day exposure period, mortality counts were taken, and the surviving insects were weighed. From the weights of the surviving insects that fed on the treated diet as compared to those insects that fed on the untreated diet, the percent growth inhibition caused by each test chemical was determined. From these data, the negative log of the concentration of the test chemical that provided 50% growth inhibition ($p1_{50}$) was determined by linear regression, when possible, for each test chemical. Where possible, the negative log of the concentration of the test chemical that provided 50% mortality ($pLC_{50}$) was determined.

Generally, the compounds of the present invention inhibited the growth of the tobacco budworm, as shown in the following table of data for selected compounds:

| No. | Rate of Application[1] | % Growth Inhibition[2] |
|---|---|---|
| 1 | 5 | 53[3] |
| 2 | 5 | 97[3] |
| 3 | 5 | 97 |
| 4 | 5 | 98 |
| 5 | 5 | 100[3] |
| 6 | 5 | 100[3] |
| 7 | 5 | 101 |
| 8 | 5 | 99 |
| 9 | 5 | 99 |
| 10 | 5 | 94 |
| 26 | 5 | 100 |
| 29 | 5 | 59 |
| 50 | 5 | 100 |
| 54 | 5 | 99 |
| 62 | 5 | 98 |
| 65 | 5 | 95 |
| 85 | 5 | 99 |
| 86 | 5 | 99 |
| 89 | 5 | 98 |
| 90 | 5 | 99 |
| 131 | 5 | 99 |
| 151 | 5 | 100 |
| 283 | 5 | 100 |
| 288 | 5 | 97 |
| 289 | 5 | 100 |
| 389 | 5 | 100 |

[1]The rate of application is expressed as the negative log og the molar concentration of the test compound in the diet.

[2]Precent growth inhibition is derived from the total weight of the insects (IW) at each rate of application in the test relative to the total weight of the insects in an untreated control:

$$\%\,Gr.\ Inh = \frac{[IW(control) - IW(test)]}{[IW(control)]} \times 100$$

[3]Average of two results

EXAMPLE 9

Insecticidal activity in foliar evaluations against the tobacco budworm.

In these tests against the tobacco budworm, nine-day-old chick pea plants (*Cicer arietinum*) were sprayed at 20 psi to runoff on both upper and lower leaf surfaces with solutions of test chemical to provide application rates as high as 1000 ppm of test chemical. The solvent used to prepare the solutions of test chemical was 10% acetone or methanol (v/v) and 0.1% of the surfactant octylphenoxypolyethanol in distilled water. Four replicates, each containing four chick pea plants, for each rate of application of test chemical were sprayed. The treated plants were transferred to a hood where they were kept until the spray had dried.

The four chick pea plants in each replicate treated with test chemical as described above were removed from their pots by cutting the stems just above the soil line. The excised leaves and stems from the four plants in each replicate were placed in individual 8-ounce paper cups, which contained a moistened filter paper. Five second-instar (4–5 days old) tobacco budworms were counted into each cup, taking care not to cause injury. An opaque plastic lid was placed on each cup, which was then held in a growth chamber for a 96 hour exposure period at 25° C. and 50% relative humidity. At the end of the 96 hour exposure period the cups were opened, and the numbers of dead and live insects were counted. Moribund larvae which were disoriented or unable to crawl normally were counted as dead. Using the insect counts, the efficacy of the test chemical was expressed in percent mortality. The condition of the test plants was also observed for phytotoxicity and for reduction of feeding damage as compared to an untreated control. Where applicable, computer- generated $LC_{50}$ values were determined from the percentages of insect mortality. The resulting data are presented in the following table:

| Cmpd No. | Rate of Application | Percent Control[1] TBW |
|---|---|---|
| 4 | 300 | 65 |
| 6 | 300 | 100 |
| 7 | 300 | 100 |
| 8 | 300 | 100 |

[1]Percent control is derived from the total number of dead insects (TD) plus the total number of moribound insects (TM) relative to the number of insects (TI) used in the test.

$$\%\,\text{Control} = \frac{TD + TM}{TI} \times 100$$

The compounds of the present invention also provide insecticidal activity in foliar evaluations against the beet armyworm (*Spodoptera exigua* [Hubner]) and the cabbage looper (*Trichoplusia ni* [Hubner]), and various other insects and acarids described above.

We claim:

1. A compound of the formula:

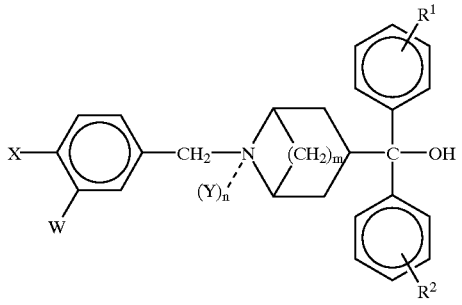

in which m is 2 or 3;

n is 0 or 1;

W is hydrogen or alkoxy;

X is hydrogen, alkoxy, cycloalkylalkoxy, alkoxycarbonyl, alkoxycarbonylamino, alkoxyimino, haloalkoxyimino, or a five-or six-membered heteroaryl or heteroaryloxy in which one or more hetero atoms may be optionally substituted with an alkyl;

$R^1$ and $R^2$ are independently selected from hydrogen, haloalkyl, halothio, or haloalkoxy; and when n is 1, Y represents (a) an N-oxide of the ring nitrogen or (b) an agriculturally acceptable anionic salt of the ring nitrogen; or (c) forms an $OR^3$ linkage in which $R^3$ is selected from hydrogen, alkyl, alkoxycarbonylalkyl, hydroxycarbonylethyl, in association with an agriculturally acceptable anion resulting in an anionic salt, or $R^3$ is an oxycarbonylalkyl group bearing a negative charge resulting in an inner salt.

2. The compound claim 1 in which W is hydrogen or propoxy, X is hydrogen, ethoxy, propoxy, butoxy, (C1–C3 alkoxy)carbonyl, (C1–C3 alkoxy)carbonylamino, 2-(C1–C2 alkyl)tetrazol-5-yl, pyridyl-2-yl, pyridyl-2-yloxy, or cyclopropylmethoxy; $R^1$ and $R^2$ are 4-trifluoromethyl or 4-trifluorormethoxy.

3. The insecticidal compounds of claim 1 in which W is hydrogen; X is propoxy, methoxycarbonylamino, or 2-ethyltetrazol-5-yl; $R^1$ and $R^2$ are 4-trifluoromethyl or 4-trifluoromethoxy; $R^3$ is methyl, ethoxycarbonylethyl, or an oxycarbonylethyl group, and the associated anionic or inner salts thereof.

4. An insecticidal composition comprising an insecticidally effective amount of the compound of claim 1 in admixture with an agriculturally acceptable diluent carrier, excipient, adjuvant or combination thereof.

5. A method for controlling insects comprising applying to a locus where control is desired an insecticidally effective amount of the compound of claim 1 or an agriculturally acceptable formulation thereof.

6. Compounds of the formula:

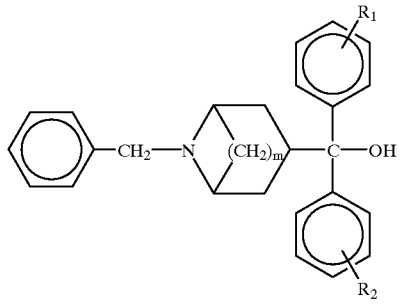

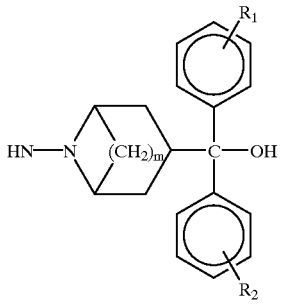

in which m is 2 or 3; and $R^1$ and $R^2$ are 4-trifluoromethyl or 4-trifluoromethoxy.

* * * * *